(12) United States Patent
Summers et al.

(10) Patent No.: US 7,790,435 B2
(45) Date of Patent: Sep. 7, 2010

(54) CHEMICAL INDUCTION IN QUIESCENCE IN BACTERIA

(75) Inventors: David Keith Summers, Cambridge (GB); Ellie Chant, Cambridge (GB)

(73) Assignee: Cambridge Microbial Technologies Limited, Cambridge (GB)

( * ) Notice: Subject to any disclaimer, the term of this patent is extended or adjusted under 35 U.S.C. 154(b) by 56 days.

(21) Appl. No.: 12/158,265

(22) PCT Filed: Dec. 18, 2006

(86) PCT No.: PCT/GB2006/004751

§ 371 (c)(1),
(2), (4) Date: Jun. 19, 2008

(87) PCT Pub. No.: WO2007/071959

PCT Pub. Date: Jun. 28, 2007

(65) Prior Publication Data

US 2009/0004700 A1  Jan. 1, 2009

(30) Foreign Application Priority Data

Dec. 20, 2005 (GB) ................................. 0525866.0

(51) Int. Cl.
*C12N 1/38* (2006.01)
(52) U.S. Cl. ................ 435/244; 435/252.33; 435/252.8
(58) Field of Classification Search ........................ None
See application file for complete search history.

(56) References Cited

U.S. PATENT DOCUMENTS 4,898,818 A * 2/1990 Nakai et al. ................. 435/69.1

FOREIGN PATENT DOCUMENTS

WO  WO 97/34996  9/1997

OTHER PUBLICATIONS

Chant et al., "Indole signaling contributes to the stable maintenance of *Escherichia coli* multicopy plasmids," *Molecular Microbiology*, 63:35-43 (2007).
Chattoraj, Dhruba K., "Tryptophanse in sRNA control of the *Escherichia coli* cell cycle," *Molecular Microbiology*, 63:1-3 (2007).
Hirakawa et al., "Indole induces the expression of multidrug exporter genes in *Escherichia coli*," *Microbiology*, 55:1113-1126 (2005).
Mukherjee et al., "Studies of single-chain antibody expression in quiescent *Escherichia coli*," *Applied and Environmental Microbiology*, 70:3005-3012 (2004).
Bass & Yansura, "Application of the *E. coli trp* Promoter," *Molecular Biotechnology*, 16:253-259, 2000.
Mizukami et al., "Production of Active Human Interferon-β in *E. coli* II. Optimal condition for induced synthesis by 3,β-indoleacrylic acid," *Biotechnology Letters*, 8(9):611-614, 1986.
Noguchi et al., "An Approach to High-Level Production of Cephalosporin Acylase from *Pseudomonas* Strain N176 in *Escherichia coli*," *J. Ferment. Bioengin*,. 85(6):634-637, 1998.

* cited by examiner

*Primary Examiner*—James S Ketter
(74) *Attorney, Agent, or Firm*—Klarquist Sparkman, LLP

(57) ABSTRACT

Quiescence is induced in cells using indole compounds. Expression continues from extra-chromosomal vectors within the cells during quiescence, while chromosomal expression is suppressed. The cells may be used as factories for the production of large amounts of polypeptides of interest, particularly polypeptides which normally have an adverse effect on cell viability or growth. Expression from an extra-chromosomal vector of interest may be monitored, in view of the reduced background expression from the chromosome. Vector copy number may be amplified. Cell cycles may be synchronized.

28 Claims, 10 Drawing Sheets

CHEMICAL INDUCTION IN QUIESCENCE IN BACTERIA

CROSS REFERENCE TO RELATED APPLICATIONS

This is the U.S. National Stage of International Application No. PCT/GB2006/004751, filed Dec. 18, 2006, which was published in English under PCT Article 21(2), which in turn claims priority to Application GB 0525866.0, filed Dec. 20, 2005. Both applications are incorporated herein in their entirety.

The present invention relates to cells in culture, in particular generation of quiescent cells. Quiescent cells have many applications in gene cloning and expression and in synchronisation of cell division. Methods and means are provided for inducing and capitalising on quiescence of cells. The present invention in various aspects and embodiments involves induction of quiescence using indole compounds.

The genetic blueprint is stored, in an encoded form, in deoxyribonucleic acid (DNA) which is a major component of chromosomes in both prokaryotic and eukaryotic organisms. The unit of information in the DNA is the gene. The majority of genes encode polypeptides whose expression requires firstly the transcription of a messenger ribonucleic acid (mRNA) and subsequent translation of the mRNA to produce the polypeptide. A subset of genes is transcribed but not translated.

The development of recombinant DNA technology over the last 30 years has made it possible to identify and isolate genes from any organism and express their products in a variety of eukaryotic and prokaryotic cell types, and in recombinant plants and animals. In vitro protein synthesis systems have also been developed. However, considerations of cost and ease of handling favour the use of bacteria and among these the most common host organism is the enteric bacterium *Escherichia coli*. Its strengths include its sophisticated genetics, the ability to grow rapidly in inexpensive media, and the availability of many customised cloning vectors (Baneyx, 1999). Inherent shortcomings of bacterial expression systems include mis-folding of multiple-domain proteins and the absence of glycosylation, although the latter is a lesser concern when proteins are required for research rather than therapeutic use.

To achieve expression of a foreign gene in a bacterium, the gene is first inserted into a small, circular DNA molecule known as a cloning vector and then introduced into the bacterium by transformation or electroporation. Cloning vectors are often derivatives of plasmids; autonomously-replicating DNA circles which are found extensively in natural populations of bacteria. Typically, vectors carry antibiotic resistance genes to facilitate selection of vector-containing cells and expression signals which direct the host bacterium to synthesise exogenous genes. The copy number of cloning vectors is often significantly higher than the copy number of the natural plasmids from which they were derived.

A number of factors may reduce the efficiency with which the products of recombinant genes are expressed in a bacterial host:

Conventional approaches express cloned genes in actively-growing cells. The cellular machinery required for transcription and translation of the recombinant gene is also required for the expression of genes essential for the growth of the host cell. There is thus a conflict between the requirements of the biotechnologist and the bacterium.

The metabolic stress imposed by the expression of a recombinant gene invariably reduces the growth rate and viability of the host cell. The higher the copy number of the cloning vector, the greater the effect. Cells which have lost the cloning vector or have deleted or rearranged the cloned gene will almost invariably out-grow the original cell-type, reducing yield and purity of the product.

Expression of the cloned gene is simultaneous with the expression of large numbers of genes located on the host chromosome. The recombinant product is therefore likely to represent a relatively small proportion of total cell protein synthesis, especially if the copy number of the cloning vector is not very high.

These problems can potentially be avoided, or at least reduced in severity, if recombinant genes are expressed in non-growing cells. The desirability of uncoupling biomass production from the expression of cloned genes stimulated interest in the basis of bacterial dormancy (Kaprelyants et al., 1993). Little is known of the transition to the dormant state but it can be induced by restricting the nutrient supply through glucose, nitrogen or phosphate limitation. Genes which have been placed under the control of starvation-inducible promoters can be expressed in slowly-growing cells. For example, recombinant β-galactosidase has been expressed from an *E. coli* promoter which is induced in response to carbon starvation. Tunner et al. (1992) and Matin (1992) described how placing of the human growth hormone gene downstream of the cstA promoter stimulated production of the recombinant protein in dense, non-growing cultures. A disadvantage of the starvation and dense-culture approaches is the limitation of nutrients which means that product is unlikely to be produced for extended periods.

In 1999 (Rowe & Summers, 1999) reported the development of a method for the generation of a non-growing but metabolically-active ("quiescent") *E. coli* culture. Quiescent Cells ("Q-Cells") is a recombinant protein expression technology which exploits non-growing *E. coli* as a cell factory. The concepts underpinning the quiescent cell system came from a study of plasmid stability which identified a short, untranslated transcript which delays the division of *E. coli* cells containing plasmid multimers (Patient & Summers, 1993; Sharpe et al., 1999). Growth arrest is achieved under culture conditions where nutrients are not limiting. It offers a radical solution to the much-debated problem of sustaining protein synthesis in the absence of rapid cell division (Flickinger & Rouse, 1993). Briefly, over-expression of Rcd (a regulatory RNA encoded by plasmid ColE1) in cells in which a cellular component which normally antagonises quiescence is disrupted, in particular hns205 or rnc14 mutant cells, is used to arrest cell growth at a desired cell density, and at a stage when the chromosome is condensed. This results in complete growth arrest after approximately 3 hours without any need for resource limitation. Cells entering the quiescent state show abnormal nucleoid condensation which results in global down-regulation of chromosomal gene expression. However, plasmid genes are unaffected and the metabolic resources of the cell are channelled towards to the expression of plasmid-borne genes. The main advantages of the Q-Cell system are:

1. Biomass production halted without nutrient limitation or the use of growth-inhibitory substances;
2. Nucleoid condensation leads to preferential expression of plasmid genes;
3. Quiescent cells are capable of both de novo transcription and translation, and they remain metabolically activity for many hours;

4. Cloning vector copy number is amplified in the non-growing cells.

See also WO97/34996, which is incorporated herein by reference. The attention of the reader of the present disclosure is drawn specifically to WO97/34996, where various explanations of and supporting evidence for applications of quiescent cells are set out, applicable also for the present invention.

Research in the Summers laboratory at Cambridge University including a series of collaborations with academic and commercial laboratories has confirmed the potential of the Q-Cell system. It has been demonstrated that the quiescent state is normally stable for at least 24 hours and the establishment of quiescence is independent of growth medium composition and culture density. Successful induction of quiescence has been achieved in shake-flask and fermenter cultures at densities up to $OD_{600}=50$. An antibody fragment produced by Q-Cells in fed-batch culture is folded correctly and secreted into the supernatant at ten times the rate seen in non-quiescent cells under equivalent growth conditions (Mukherjee et al., 2004). However, the work has also identified a number of potential difficulties in using the Q-Cells expression system.
1. The Q-Cell expression strain must be freshly constructed for each use and care is needed to avoid premature expression of Rcd. This can cause problems for users who are not skilled in microbiology.
2. Quiescent cultures sometimes "escape" (i.e. they resume growth and continue into a conventional stationary phase) with the result that the advantage of the quiescent state is lost.
3. A heat shock promoter has been used to achieve reliable control over Rcd expression. This has the disadvantage that recombinant protein is expressed at 42° C.

The present invention provides a new way to create quiescent bacteria, especially *E. coli*, which overcomes these difficulties. Using this method, a quiescent bacterial culture is simple to establish, independent of temperature, and stable.

Previously, quiescent *E. coli* have been created by over-expression of the Rcd transcript in a cells in which a cellular component which normally antagonises quiescence is disrupted. Such disruption may be by virtue of a mutation in a gene for the cellular component or otherwise by provision of a suitable genetic background. Preferred has been the use of hns205 cells or rnc14 cells. For several years the Summers laboratory has been seeking the target of the Rcd transcript. As noted in Sharpe et al., 1999, the structure of Rcd suggested a hypothesis that Rcd acts as an anti-sense RNA, but the reported failure to find an RNA target led to speculation of an alternative mechanism of action with direct interaction between Rcd and a protein involved in cell division or its regulation. None of the experimental results which have now led to the identification of the target is in the public domain.

We now report for the first time that we have identified tryptophanase as a potential target, based on analysis of proteins from an *E. coli* crude lysate which were retained on an Rcd-bound column.

Tryptophanase converts tryptophan to indole which is known to act as a signalling molecule in *E. coli* (Wang et al., 2001). Cells deficient in the Rcd target should be resistant to the inhibition of colony formation on solid medium which results from Rcd over-expression. This was shown by us to be the case for a tryptophanase knockout strain of *E. coli* which was insensitive to extremely high levels of Rcd. Subsequently we demonstrated that an increased level of intracellular indole results when Rcd is expressed in response to multimerization of a cer$^+$ plasmid, or when the Rcd is expressed from an independently-regulated promoter such as $P_{lac}$. Evidence for a direct interaction between Rcd and tryptophanase was provided by our unpublished observation that, in an in vitro assay using purified components, Rcd increases the affinity of tryptophanase for its substrate (tryptophan) approximately four-fold.

We have now established that the addition of indole to broth cultures of *E. coli* induces quiescence. Experimentation is described below. We have coined the term "chemical Q cells" or "cQC" to describe cells made quiescent in accordance with the present invention.

A growth-inhibitory effect of indole is disclosed by *Journal of Antibiotics* (Tokyo) 1974 27 (12) 987-988.

BRIEF DESCRIPTION OF THE FIGURES

FIG. 3 shows that an indole-induced quiescent state can be induced at a range of culture temperatures.

FIG. 4 shows that indole-induced quiescent cultures of W3110hns205 can express the cytokine hGM-CSF.

FIG. 5 shows that indole-induced quiescent cultures of W3110hns205 can express beta-galactosidase (LacZ).

(closed diamonds, 0 mM indole; closed circles, 0 mM indole+ ethanol 0.6%; closed squares, 3 mM indole; open circles, 3 mM isoquinoline; closed triangles, 3 mM indoline)

Figure 9:
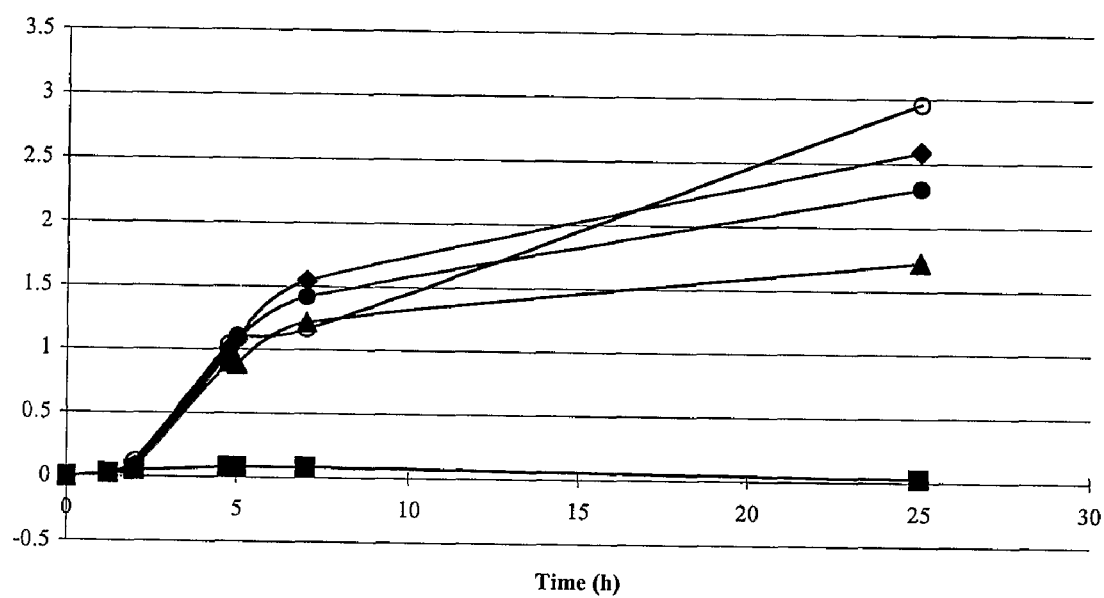

FIG. 9 shows the effect of 3 mM indole, tryptamine, and IAA on W3110hns-205::Tn10. Growth in L-broth containing tetracycline was monitored by measuring $OD_{600}$ of culture samples. A control (ethanol, 0.6%) was included to ensure that the ethanol used to prepare stock solutions of indole and indole-related compounds was not affecting growth. Data plotted are the mean of two independent assays. (closed diamonds, 0 mM indole; closed circles, 0 mM indole+ethanol 0.6%; closed squares, 3 mM indole; open circles, 3 mM IAA; closed triangles, 3 mM tryptamine).

Figure 10:
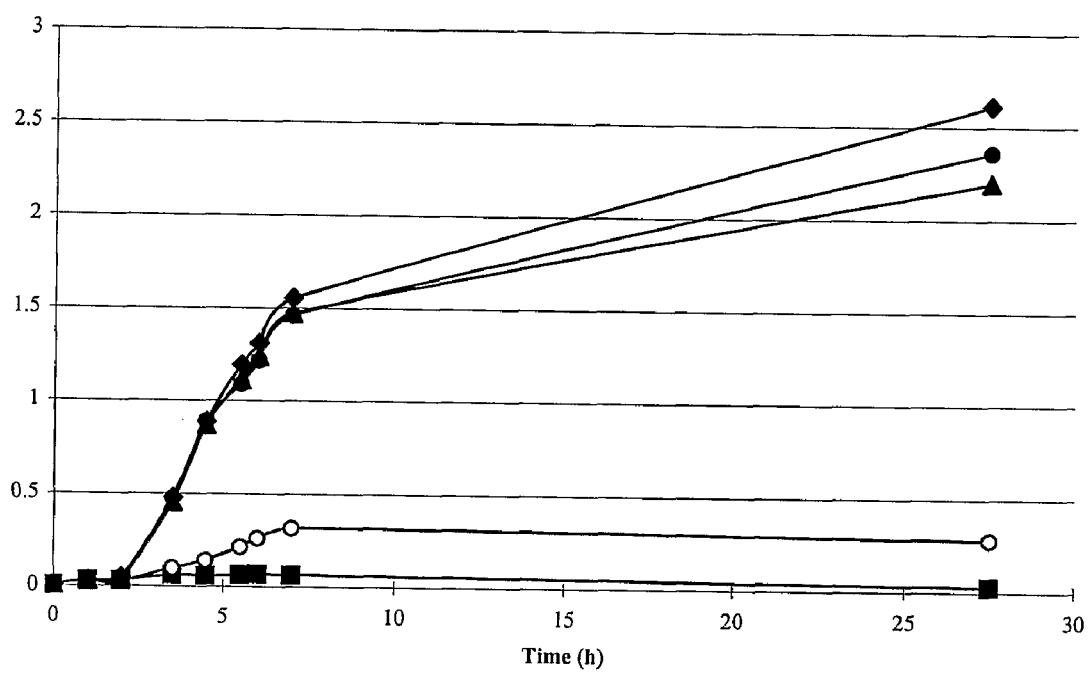

FIG. 10 shows the effect of 3 mM indole, quinoline, and pyrrole on W3110hns-205::Tn10. Growth in L-broth plus tetracycline was monitored by measuring $OD_{600}$ of culture samples. A control (ethanol, 0.6%) was included to ensure that the ethanol used to prepare stock solutions of indole and indole-related compounds was not affecting growth. Data plotted are the mean of two independent assays (T: tetracycline). (closed diamonds, 0 mM indole; closed circles, 0 mM indole+ethanol 0.6%; closed squares, 3 mM indole; open circles, 3 mM quinoline; closed triangles, 3 mM pyrrole).

Figure 11:
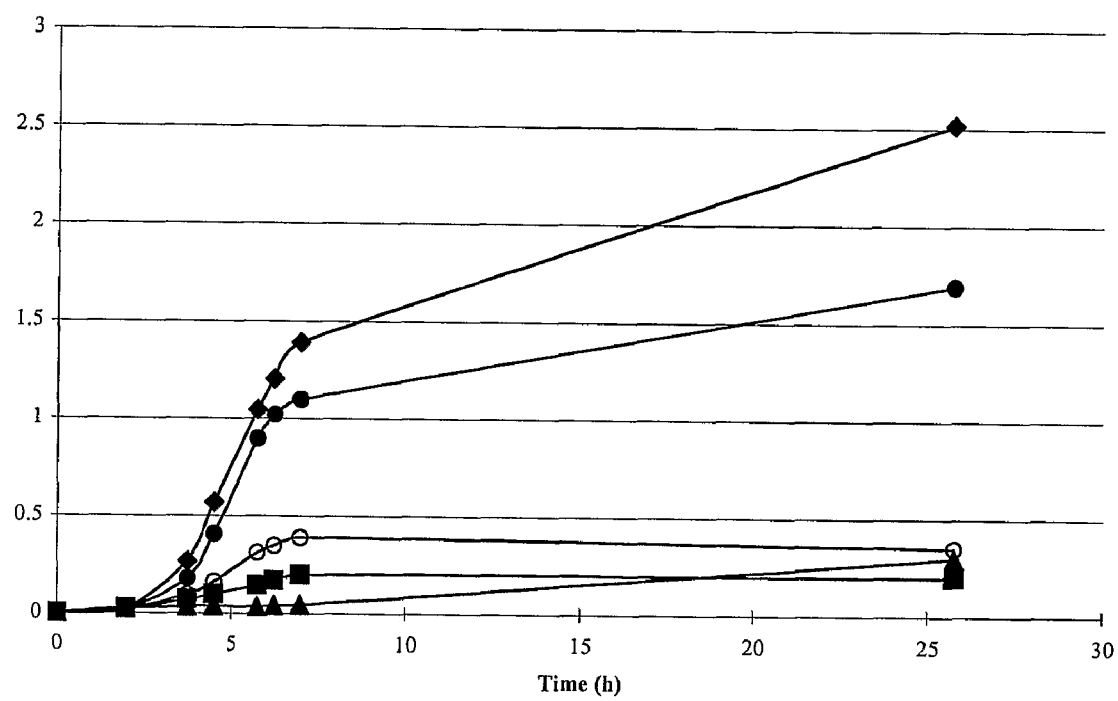

FIG. 11 shows the effect of 3 mM indole, 3-beta-indoleacrylic acid, and 1-acetylindoline on W3110hns-205::Tn10. Growth in L-broth plus tetracycline was monitored by measuring $OD_{600}$ of culture samples. A control (ethanol, 2.4%) was included to ensure that the ethanol used to prepare stock solutions of indole and indole-related compounds was not affecting growth. Data plotted are the mean of two independent assays (T: tetracycline). (closed diamonds, 0 mM indole; closed circles, 0 mM indole+ethanol 2.4%; closed squares, 3 mM indole; open circles, 3 mM 1-acetylindoline; closed triangles, 3 mM 3-beta-indoleacrylic acid).

The present invention is founded on the discovery that indole can inhibit the growth of cells in broth culture when the cells are disrupted in a cellular component which normally antagonises quiescence, for example cells that are hns⁻, i.e. lack or have a defective hns gene. The roles of H-NS protein are reviewed by Ussery et al (1994). The sequence of H-NS is given in: Pon, et al., *Mol. Gen. Genet.* 212, 199-202. Nomenclature has settled on hns but at some places in the literature the gene is also referred to as: hnsA, bglY, drdX, msyA, osmZ and pilG. Bacteria other than *E. coli* have H-NS-related proteins for which sequences have been published, for example *S. Flexneri, S. typhimurium, S. marcescens* and *P. vulgaris*. The present invention is not limited to *E. coli* and may be applied to any bacterial species, so references to hns⁻ cells should be taken as reference to cells defective or deficient in the relevant hns like gene in the bacteria of interest.

Equivalent genes or homologues in other bacteria may be identified using any of a number of available approaches. H-NS-like proteins may be identified by DNA and/or amino acid sequence similarity to the *E. coli* gene or protein or homologues which have been identified already in other bacteria species (see above).

Nucleic acid and/or amino acid sequence information for HN—S or a homologue of either may be used in design of nucleic acid molecules for hybridisation experiments to identify equivalent genes or homologues. Hybridisation may involve probing nucleic acid and identifying positive hybridisation under suitably stringent conditions (in accordance with known techniques) and/or use of oligonucleotides as primers in a method of nucleic acid amplification, such as PCR. For probing, preferred conditions are those which are stringent enough for there to be a simple pattern with a small number of hybridisations identified as positive which can be investigated further. It is well known in the art to increase stringency of hybridisation gradually until only a few positive clones remain.

As an alternative to probing, though still employing nucleic acid hybridisation, oligonucleotides designed to amplify DNA sequences may be used in PCR or other methods involving amplification of nucleic acid, using routine procedures. See for instance "PCR protocols; A Guide to Methods and Applications", Eds. Innis et al, 1990, Academic Press, New York.

Preferred amino acid sequences suitable for use in the design of probes or PCR primers are sequences conserved (completely, substantially or partly) between at least two known or putative homologues. On the basis of amino acid sequence information oligonucleotide probes or primers may be designed, taking into account the degeneracy of the genetic code, and, where appropriate, codon usage of the organism from the candidate nucleic acid is derived.

Preferred nucleic acid sequences suitable for use in the design of probes or PCR primers are sequences conserved (completely, substantially or partly) between at least two known or putative homologues.

Assessment of whether or not a PCR product corresponds to an H-NS-like gene may be conducted in various ways. A PCR band from such a reaction might contain a complex mix of products. Individual products may be cloned and each one individually screened for activity.

A further method of using a sequence to identify other homologues is to use computer searches of expressed sequence tag (EST) and other DNA sequence databases.

Wild-type H-NS (the product of the hns gene) antagonises the establishment and/or maintenance of quiescence in bacterial cells in broth. Experimental evidence demonstrates with various hns⁻ alleles, especially truncation alleles, that hns⁻ cells in broth culture enter quiescence on expression of Rcd (See WO97/34996) and on treatment with indole. Illustrative truncated alleles include hns-205 and hns_Tn10(N43). In both cases the C-terminal part of the H-NS protein is absent due to a transposon insertion in the gene. The 205 allele is described in detail in Dersch, et al., *Mol. Gen. Genet.* (1994) 245, 255-259. The N43 strain was given to us by Prof. I. B. Holland, Université Paris-Sud. The hns-206_Amp allele also used is described in detail in Dersch, et al., *Mol. Gen. Genet.* (1994) 245, 255-259. In this case there is no detectable protein product.

As noted, the sequence of *E. coli* H-NS is given in Pon et al. (1988) *Mol. Gen. Genet.* 212 199-202. The present invention may utilise down-regulation of or a mutation in this gene in *E. coli* or in an allele or homologue in other bacterium. An allele or homologue may share a certain level of homology with the sequence of *E. coli* H-NS. Homology may be at the nucleotide sequence and/or amino acid sequence level. In some embodiments, the nucleic acid and/or amino acid sequence shares homology with the sequence encoded by the nucleotide sequence of *E. coli* H-NS, preferably at least about 50%, or 60%, or 70%, or 80% homology, most preferably at least 90% or 95% homology. The wild-type gene shares with the *E. coli* gene the ability to antagonise the establishment and/or maintenance of quiescence in a bacterial cell, e.g. an *E. coli* cell, in broth culture. A mutant of the wild-type that abolishes, wholly or partially, this ability may be useful in the present invention.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403-10, which is in standard use in the art. Homology may be over the full-length of the H-NS sequence, or may be over a contiguous sequence of amino acids e.g. about 20, 25, 30, 40, 50 or more amino acids compared with the sequence of Pon et al. At the nucleic acid level, homology may be over the full-length or may be over a contiguous sequence of nucleotides, e.g. about, 50, 60, 70, 75, 80, 90, 100, 120, 150 or more nucleotides.

Those skilled in the art are well aware of methods which can be employed to generate hns⁻ or other mutant strains of *E. coli* or equivalents for other bacteria. One well-known technique which is particularly suitable is the use of "P1 transduction" (Miller 1972) to move transposon-inactivated hns. The technique involves introducing into host cells, via phage P1 infection, a defective hns gene containing an inserted transposon which includes a selectable marker (e.g. a gene which confers antibiotic resistance). Recombination within cells results in the replacement of the wild-type hns gene with the transposon-inactivated gene. Selection for the marker enables identification of successful recombination events. Only when the transposon is inserted into the host chromosome is the host positive for the marker. Selected cells are tested for H-NS⁻ phenotype and suitability for use in the present invention (Rcd sensitivity).

Without wishing to be bound by theory, it can be hypothesized that H-NS is required for recovery of cells from Rcd- or indole-induced growth inhibition, such that over-expression of Rcd or treatment with an indole compound in an hns mutant background pushes the cells into a non-growing state from which they have no escape. Disruption of other cellular components which normally antagonise the establishment and/or maintenance of quiescence in bacterial cells in broth on treatment with indole or an indole compound may be used in embodiments of the various aspects of the present invention instead of hns⁻.

Mutations which disrupt the antagonistic effect of a cellular component may be screened for by indole treatment or over-expressing Rcd in mutagenised wild-type cells then treating the cells (e.g. three to six hours after indole or Rcd induction) with an antibiotic such as penicillin or other molecule which kills growing cells but not cells which are not growing. Cycling this treatment several times selects for any host cell mutation which increases the severity of Rcd- or indole-mediated growth inhibition.

Another mutation which diminishes an activity which antagonises Rcd-mediated establishment and/or maintenance of quiescence in a bacterial cell in broth culture is an rnc mutation, i.e. RNase III deficiency. The effect may be direct or indirect. RNase III or one or more other endoribonucleases are responsible for Rcd turnover. Reducing the endoribonuclease activity responsible for degrading Rcd may be used to increase levels of Rcd expression and tip the balance towards establishment of quiescence in accordance with the present invention. RNase III cleaves double-stranded RNA and appears to specifically recognize stem-loop structures (Court, 1993). Much work has been done on the factors which make transcripts more or less sensitive to the enzyme (see, for example, Hjalt and Wagner, 1995). RNase E has been shown to cleave several antisense RNAs including RNAI (Tomcsányi and Apirion, 1985) and CopA (Söderbom et al., 1996). The exoribonucleases polynucleotide phosphorylase (PN-Pase) and RNase II, also have key roles in RNA decay (Donovan and Kushner, 1986). Poly (A) polymerase (PcnB), which catalyzes the template-independent sequential addition of AMP to the 3'-terminal hydroxyl groups of RNA molecules, has also been implicated in degradation of RNAI (the replication inhibitor of plasmid ColE1). RNAI undergoes PcnB-dependent polyadenylation in vivo and is rapidly degraded, subsequent to RNase E cleavage, in the presence of PcnB and PNPase (Xu et al., 1993). If the pcnB gene is inactivated, the processed species is stabilized.

Using a bacterial strain containing a mutation in a cellular component which in wild-type form antagonises the establishment and/or maintenance of quiescence in broth culture on expression of Rcd or treatment with indole is one approach in accordance with the present invention. Other ways of antagonising the function or activity of such a cellular component include down-regulation of gene expression, e.g. using antisense technology, a sequence-specific ribozyme or a modified sigma factor.

The essence of a preferred embodiment of one aspect of the invention is that by treatment with an indole compound, hns⁻ host cells, or other cells in which an activity which normally antagonises establishment of quiescence in bacterial cells in broth culture is abolished, wholly or partially, can in broth culture be switched to a quiescent state in which their growth and division is arrested. In this state the cells may produce predominantly or only the products of vector-encoded genes and with the resources required for high-level expression of extra-chromosomal genes being readily available. This is useful in both preparative and analytical synthesis of the products of cloned genes.

The cell may comprise the vector following transformation of the cell or an ancestor thereof.

According to one aspect of the present invention there is provided a host cell treated with an indole compound, which cell when in broth culture enters quiescence. A preferred embodiment may employ a hns⁻ cell. Other cellular backgrounds, such as mutations, which reduce, diminish or decrease, wholly or partially, activity of a cellular component which antagonises the establishment of quiescence in a bacterial cell in broth culture on treatment with indole or an indole compound may be used instead of hns mutant cells. This should be borne in mind when considering the discussion herein that uses hns mutants as a preferred example. Other backgrounds, including other mutations and systems in which activity of a cellular component is antagonised, e.g. using antisense, ribozyme or other techniques at the disposal of the person skilled in the art, may be substituted for hns in the discussion herein.

The term "indole" herein, unless context requires, may be used to refer to indole itself and may also be used to refer other indole compounds. Useful in the various aspects and embodiments of the present invention as disclosed herein are indole compounds that share with indole the ability to induce quiescence in bacterial cells, such as *E. coli*, especially in cells which contain a cellular component of which wild-type activity to antagonise quiescence is disrupted, such as cells that are hns⁻ or have a rnc mutation.

Reference to an "indole compound" herein, unless context requires, should be taken to refer to any member of a class of nitrogen-containing heterocyclic compounds that comprise a structural framework based on the indan carbocyclic ring framework, where one of the carbon atoms in the framework is replaced by a nitrogen atom. The indan ring structure consists of a phenyl or benzene ring fused at one side to the side of a five membered cyclopentane ring (see below).

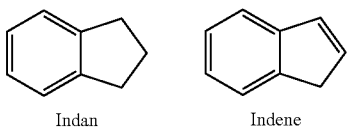

Indan    Indene

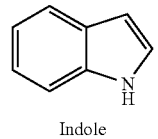

Indole

The term "indan carbocyclic ring framework" herein refers to the carbocyclic ring structure of indan or indene. At the side where the five membered ring is fused to the benzene ring, there is an unsaturated bond. However, the other bonds in the five membered carbocyclic ring may be saturated, such as in indan, or unsaturated, as in indene. Examples of indole compounds where the five membered ring is saturated (indoline) or is unsaturated and contains a double bond (3-H indole), in addition to the bond where the benzene ring is fused to the five membered ring, are shown below.

The unsaturated bond may form part of a second fused ring, such as in the indole compound known in the art as carbazole (see below).

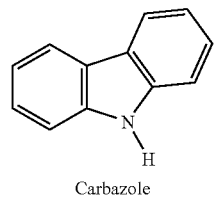

Carbazole

The term indole compound is preferred to refer to compounds based on an indan carbocyclic ring framework that does not contain an additional ring fused to this carbocyclic ring framework, such as the second benzene ring in carbazole above. In particular embodiments, the term indole compound refers to the subset of compounds where the nitrogen atom itself is outside of and directly bonded to the benzene ring i.e. the nitrogen atom is in the 1 or 3 positions.

The class of compounds represented by the term indole compound as used herein may be represented by the general formula (I):

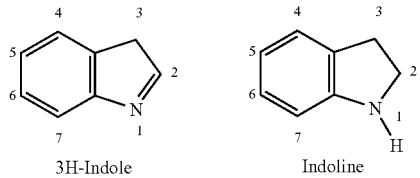

3H-Indole    Indoline

The term indole compound is not limited by the identity of the substituents attached to the rings. An indole compound may contain one or more substituents or may be completely unsubstituted.

More specifically, the term indole compound refers to a class of compounds where the nitrogen forms part of the five membered ring. The term indole compound may take a narrower meaning by referring to those compounds where the nitrogen atom does not form part of the unsaturated six membered ring. In such compounds, the nitrogen atom may be bonded to the benzene ring or positioned so that it is not directly bonded to the benzene, such as 1H-isoindole where the nitrogen atom is in the 2-position, as shown using the standard numbering scheme for the indan carbocyclic framework below.

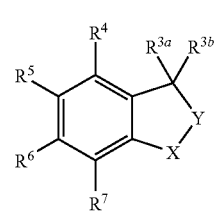 (I)

wherein

X—Y represents

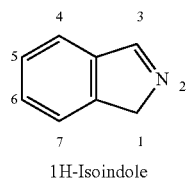

1H-Isoindole

If the five membered ring contains an unsaturated bond, in addition to that provided by the fused benzene ring, then the unsaturated bond is position between the 1,2 positions, such as in 3H-indole, or between the 2,3 positions, as in the compound referred to in the art as indole.

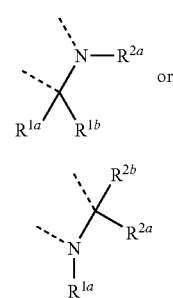

and (i) $R^{1a}$, $R^{1b}$, $R^{2a}$, $R^{2b}$, $R^{3a}$, $R^{3b}$, $R^4$, $R^5$, $R^6$ and $R^7$ are each independently selected from biologically compatible substituents; or (ii) $R^{2b}$ and $R^{3b}$ together form double bond or are linked to form an optionally substituted benzene ring, and $R^{1a}$, $R^{1b}$, $R^{2a}$, $R^{3a}$, $R^4$, $R^5$, $R^6$ and $R^7$ are each independently selected from biologically compatible substituents; or (iii) in (A), $R^{1b}$ and $R^{2a}$ together form a double bond or are linked to form an optionally substituted benzene ring, and $R^{1a}$, $R^{2b}$, $R^{3a}$, $R^{3b}$, $R^4$, $R^5$, $R^6$ and $R^7$ are each independently selected from biologically compatible substituents.

The term "biologically compatible substituent" as used herein pertains to an atom or chemical functional group that is covalently bonded to the structure represent by general formula (I) above at the positions $R^{1a}$, $R^{1b}$, $R^{2a}$, $R^{2b}$, $R^{3a}$, $R^{3b}$, $R^4$, $R^5$, $R^6$ and $R^7$ such that the resulting molecule is compatible with the cells retaining ability to express genes from extra-chromosomal vectors, even if there is some toxicity to the cells (especially if at high concentrations). Biologically compatible substituents may be any substituent selected from the list of substituents presented below.

Typically, the term indole compound refers to a class of compounds having a double bond in the five membered ring. In particular embodiments this term refers to those compounds where $R^{1b}$ and $R^{2a}$, or $R^{2b}$ and $R^{3b}$ together form a double bond.

More specifically, the term indole compound refers to a class of compounds represented by general formula (I) where X—Y is given by the structural fragment (B).

In particular, biologically compatible substituents include H, halo, hydroxyl, H, halo, hydroxyl, amino, formyl, carboxy, nitro, nitroso, azido, cyano, isocyano, cyanato, isocyanato, thiocyano, isothiocyano, sulfhydryl, sulfonic acid and the optionally substituted substituents alkyl, aryl, heterocyclyl, ether, acyl, acyl halide, ester, acyloxy, amido, acylamido, thioamido, thioether, sulfonate, sulfone, sulfonyloxy, sulfinyloxy, sulfamino, sulfonamino, sulfinamino, sulfamyl and sulfonamido.

The optionally substituted alkyl group may be an $C_{1-7}$alkyl, the heterocyclyl group may be $C_{3-20}$heterocyclyl and the aryl group may be $C_{5-20}$aryl. Further biologically compatible substituents are H, halo, hydroxyl, amino, formyl, carboxy, nitro, sulfhydryl, and the optionally substituted substituents $C_{1-7}$alkyl, $C_{3-20}$heterocyclyl, $C_{5-20}$aryl, $C_{1-7}$alkoxy, $C_{6-10}$aryloxy, acyl, ester (R=$C_{1-7}$ alkyl or $C_{6-10}$aryl), acyloxy, amido, acylamido, $C_{1-7}$alkylthio and $C_{6-10}$arylthio.

For substituents that may be optionally substituted, the optional substituents may be selected from halo, hydroxyl, amino, formyl, carboxy, nitro, nitroso, azido, cyano, isocyano, cyanato, isocyanato, thiocyano, isothiocyano, sulfhydryl, sulfonic acid, $C_{1-7}$alkyl, $C_{3-20}$heterocyclyl, $C_{5-20}$aryl, $C_{1-7}$alkoxy, $C_{6-10}$aryloxy, acyl, ester (R=$C_{1-7}$ alkyl or $C_{6-10}$aryl), acyloxy, amido, acylamido, $C_{1-7}$alkylthio, $C_{6-10}$arylthio, acyl, acyl halide, acyloxy, amido, acylamido, thioamido, sulfonate, sulfone, sulfonyloxy, sulfinyloxy, sulfamino, sulfonamino, sulfinamino, sulfamyl and sulfonamido. More preferred optional substituents are halo, hydroxyl, amino, carboxy, $C_{1-7}$alkyl, $C_{5-20}$aryl, $C_{1-7}$alkoxy and $C_{6-10}$aryloxy.

The most preferred substituent for nitrogen ($R^{2a}$ or $R^{1a}$ in structural fragments (A) and (B) respectively, above). H is the most preferred substituent for any of $R^{1a}$, $R^{1b}$, $R^{2a}$, $R^{2b}$, $R^{3a}$, $R^{3b}$, $R^4$, $R^5$, $R^6$ and $R^7$.

As will be appreciated by the skilled artisan, the above structure is one of many possible resonance structures which may be drawn to depict the same compound. As used herein, and unless otherwise specified, a reference to one structure is to be considered a reference to all possible corresponding resonance structures.

Phenyl Groups

Examples of phenyl substituents, $R^4$ through $R^7$, include, but are not limited to those discussed below under the heading "substituents."

If the phenyl group has less than the full complement of substituents, they may be arranged in any combination. For example, if the phenyl group has a single substituent other than hydrogen, it may be in the $R^4$, $R^5$, $R^6$ or $R^7$ position. Similarly, if the phenyl group has two substituents other than hydrogen, they may be in the $R^4$, $R^5$, the $R^4$, $R^6$, the $R^4$, $R^7$, the $R^5$, $R^6$, the $R^5$, $R^7$, or the $R^6$, $R^7$ positions. If the phenyl group has three substituents other than hydrogen, they may be in, for example, the $R^4$, $R^5$, $R^6$ or the $R^4$, $R^5$, $R^7$, or the $R^4$, $R^6$, $R^7$ or $R^8$, $R^6$, $R^7$ positions.

In one group of embodiments, the phenyl group has only one substituent other than hydrogen, which is in the $R^4$, $R^5$, $R^6$, or $R^7$ position.

Adjacent Substituents May be Linked to Form a Ring

The possibility that substituents adjacent to one another, for example $R^4$ and $R^5$ or $R^{2b}$ and $R^{3b}$, together (including the carbon atoms to which they are attached) form a cyclic structure is not excluded. For example, the substituents, $R^{2b}$ and $R^{3b}$, together with the carbon atoms to which they are attached, may form a fused ring structure, such as the benzene ring found in carbazole (see above). It is desirable that adjacent substituents do not link to form a cyclic structure.

Chemical Terms

The term "saturated", as used herein, pertains to compounds and/or groups which do not have any carbon-carbon or carbon nitrogen double or triple bonds.

The term "unsaturated", as used herein, pertains to compounds and/or groups which have at least one carbon-carbon or carbon-nitrogen double bond or carbon-carbon triple bond. Compounds and/or groups may be partially unsaturated or fully unsaturated.

The term "aliphatic", as used herein, pertains to compounds and/or groups which are linear or branched, but not cyclic (also known as "acyclic" or "open-chain" groups).

The term "ring", as used herein, pertains to a closed ring of covalently linked ring atoms, which may be an alicyclic ring or an aromatic ring. The term "alicyclic ring," as used herein, pertains to a ring which is not an aromatic ring.

The term "carbocyclic ring," as used herein, pertains to a ring wherein all of the ring atoms are carbon atoms.

The term "carboaromatic ring", as used herein, pertains to an aromatic ring wherein all of the ring atoms are carbon atoms.

The term "heterocyclic ring", as used herein, pertains to a ring wherein at least one of the ring atoms is a multivalent ring heteroatom, for example, nitrogen, phosphorus, silicon, oxygen, or sulfur, though more commonly nitrogen, oxygen, or sulfur. The heterocyclic ring may have from 1 to 4 ring heteroatoms.

The term "cyclic compound", as used herein, pertains to a compound which has at least one ring. The term "cyclyl," as used herein, pertains to a monovalent moiety obtained by removing a hydrogen atom from a ring atom of a cyclic compound.

Substituents

The phrase "optionally substituted," as used herein, pertains to a parent group which may be unsubstituted or which may be substituted.

Unless otherwise specified, the term "substituted," as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

Alkyl: The term "alkyl" as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g., partially unsaturated, fully unsaturated). Thus, the term "alkyl" includes the sub-classes alkenyl, alkynyl, cycloalkyl, cycloalkyenyl, cylcoalkynyl, etc., discussed below.

In the context of alkyl groups, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl," as used herein, pertains to an alkyl group having from 1 to 4 carbon atoms. Examples of groups of alkyl groups include $C_{1-4}$alkyl ("lower alkyl"), $C_{1-7}$alkyl, and $C_{1-20}$alkyl. Note that the first prefix may vary according to other limitations; for example, for unsaturated alkyl groups, the first prefix must be at least 2; for cyclic and branched alkyl groups, the first prefix must be at least 3; etc.

Examples of (unsubstituted) saturated alkyl groups include, but are not limited to, methyl ($C_1$), ethyl ($C_2$), propyl ($C_3$), butyl ($C_4$), pentyl ($C_5$) and hexyl ($C_6$).

Examples of (unsubstituted) saturated linear alkyl groups include, but are not limited to, methyl ($C_1$), ethyl ($C_2$), n-propyl ($C_3$), n-butyl ($C_4$), and n-pentyl (amyl) ($C_5$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl" as used herein, pertains to an alkyl group having one or more carbon-carbon double bonds. Examples of groups of alkenyl groups include $C_{2-4}$alkenyl, $C_{2-7}$alkenyl, $C_{2-20}$alkenyl.

Examples of (unsubstituted) unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$) and isopropenyl (1-methylvinyl, —C(CH$_3$)=CH$_2$).

Alkynyl: The term "alkynyl" as used herein, pertains to an alkyl group having one or more carbon-carbon triple bonds. Examples of groups of alkynyl groups include $C_{2-4}$alkynyl, $C_{2-7}$alkynyl and $C_{2-20}$alkynyl.

Examples of (unsubstituted) unsaturated alkynyl groups include, but are not limited to, ethynyl (ethinyl, —C≡CH) and 2-propynyl (propargyl, —CH$_2$—C≡CH).

Cycloalkyl: The term "cycloalkyl" as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g., partially unsaturated, fully unsaturated), which moiety has from 3 to 20 carbon atoms (unless otherwise specified), including from 3 to 20 ring atoms. Thus, the term "cycloalkyl" includes the sub-classes cycloalkyenyl and cycloalkynyl. In some embodiments, each ring has from 3 to 7 ring atoms. Examples of groups of cycloalkyl groups include $C_{3-20}$cycloalkyl, $C_{3-15}$cycloalkyl, $C_{3-10}$cycloalkyl, $C_{3-7}$cycloalkyl.

Examples of cycloalkyl groups include, but are not limited to, those derived from:

saturated monocyclic hydrocarbon compounds: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$) and methylcyclobutane ($C_5$);

unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$);

saturated polycyclic hydrocarbon compounds: norpinane ($C_7$), norbornane ($C_7$), adamantane ($C_{10}$), decalin ($C_{10}$);

unsaturated polycyclic hydrocarbon compounds: camphene ($C_{10}$), limonene ($C_{10}$), pinene ($C_{10}$);

polycyclic hydrocarbon compounds having an aromatic ring: indene ($C_9$), indane ($C_9$), tetraline (1,2,3,4-tetrahydronaphthalene) ($C_{10}$C), acenaphthene ($C_{12}$) and fluorene ($C_{13}$).

Alkylidene: The term "alkylidene," as used herein, pertains to a divalent monodentate moiety obtained by removing two hydrogen atoms from an aliphatic or alicyclic carbon atom of a hydrocarbon compound having from 1 to 20 carbon atoms (unless otherwise specified). Examples of groups of alkylidene groups include $C_{1-20}$alkylidene, $C_{1-7}$alkylidene, $C_{1-4}$alkylidene.

Examples of alkylidene groups include, but are not limited to, methylidene (=CH$_2$), ethylidene (=CH—CH$_3$), vinylidene (=C=CH$_2$), isopropylidene (=C(CH$_3$)$_2$), cyclopentylidene, and benzylidene (=CH-Ph).

Alkylidyne: The term "alkylidyne" as used herein, pertains to a trivalent monodentate moiety obtained by removing three hydrogen atoms from an aliphatic or alicyclic carbon atom of a hydrocarbon compound having from 1 to 20 carbon atoms (unless otherwise specified). Examples of groups of alkylidyne groups include $C_{1-20}$alkylidyne, $C_{1-7}$alkylidyne, $C_{1-4}$alkylidyne.

Examples of alkylidyne groups include, but are not limited to, methylidyne (≡CH), ethylidyne (≡C—CH$_3$), and benzylidyne (≡C-Ph).

Carbocyclyl: The term "carbocyclyl" as used herein, pertains to a monovalent moiety obtained by removing a hydrogen atom from a ring atom of a carbocyclic compound, which moiety has from 3 to 20 ring atoms (unless otherwise specified). In some embodiments, each ring has from 3 to 7 ring atoms.

In this context, the prefixes (e.g., $C_{3-20}$, $C_{3-7}$, $C_{5-6}$, etc.) denote the number of ring atoms, or range of number of ring atoms. For example, the term "$C_{5-6}$carbocyclyl," as used herein, pertains to a carbocyclyl group having 5 or 6 ring atoms. Examples of groups of carbocyclyl groups include $C_{3-20}$carbocyclyl, $C_{3-10}$carbocyclyl, $C_{5-10}$carbocyclyl, $C_{3-7}$carbocyclyl, and $C_{5-7}$carbocyclyl.

Examples of carbocyclic groups include, but are not limited to, those described above as cycloalkyl groups; and those described below as carboaryl groups.

Heterocyclyl: The term "heterocyclyl" as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. In some embodiments, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl" as used herein, pertains to a heterocyclyl group having 5 or 6 ring atoms.

Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose and mannopyranose.

Examples of heterocyclyl groups which are also heteroaryl groups are described below with aryl groups.

Aryl: The term "aryl" as used herein, pertains to a monovalent moiety obtained by removing a hydrogen atom from an aromatic ring atom of an aromatic compound, which moiety has from 3 to 20 ring atoms (unless otherwise specified). In some embodiments, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{3-20}$aryl, $C_{5-20}$aryl, $C_{5-15}$aryl, $C_{5-12}$aryl, $C_{5-10}$aryl, $C_{5-7}$aryl, $C_{5-6}$aryl, $C_5$aryl, and $C_6$aryl.

The ring atoms may be all carbon atoms, as in "carboaryl groups." Examples of carboaryl groups include $C_{3-20}$carboaryl, $C_{5-20}$carboaryl, $C_{5-15}$carboaryl, $C_{5-12}$carboaryl, $C_{5-10}$carboaryl, $C_{5-7}$carboaryl, $C_{5-6}$carboaryl, $C_5$carboaryl, and $C_6$carboaryl.

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups." Examples of heteroaryl groups include $C_{3-20}$heteroaryl, $C_{5-20}$heteroaryl, $C_{5-15}$heteroaryl, $C_{5-12}$heteroaryl, $C_{5-10}$heteroaryl, $C_{5-7}$heteroaryl, $C_{5-6}$heteroaryl, $C_5$heteroaryl, and $C_6$heteroaryl.

Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heterocyclic groups (some of which are also heteroaryl groups) which comprise fused rings, include, but are not limited to:

$C_9$heterocyclic groups (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$heterocyclic groups (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$heterocyclic groups (with 2 fused rings) derived from benzodiazepine ($N_2$);

$C_{13}$heterocyclic groups (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$heterocyclic groups (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methylpyrrole. Examples of N-substitutents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N= group may be substituted in the form of an N-oxide, that is, as —N(→O)= (also denoted —N⁺(→O⁻)=). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (=O) groups on ring carbon atoms.

Monocyclic examples of such groups include, but are not limited to, those derived from:

$C_5$: cyclopentanone, cyclopentenone, cyclopentadienone;

$C_6$: cyclohexanone, cyclohexenone, cyclohexadienone;

$O_1$: furanone ($C_5$), pyrone ($C_6$);

$N_1$: pyrrolidone (pyrrolidinone) ($C_5$), piperidinone (piperidone) ($C_6$), piperidinedione ($C_6$);

$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);

$N_1S_1$: thiazolone ($C_5$), isothiazolone ($C_5$);

$N_1O_1$: oxazolinone ($C_5$).

Polycyclic examples of such groups include, but are not limited to, those derived from:

$C_9$: indenedione;
$C_{10}$: tetralone, decalone;
$C_{14}$: anthrone, phenanthrone;
$N_1$: oxindole ($C_9$);
$O_1$: benzopyrone (e.g., coumarin, isocoumarin, chromone) ($C_{10}$);
$N_1O_1$: benzoxazolinone ($C_9$), benzoxazolinone ($C_{10}$);
$N_2$: quinazolinedione ($C_{10}$); benzodiazepinone ($C_{11}$); bezodiazepinedione ($C_{11}$);
$N_4$: purinone ($C_9$) (e.g., guanine).

Still more examples of cyclic groups which bear one or more oxo (=O) groups on ring carbon atoms include, but are not limited to, those derived from:

cyclic anhydrides (—C(=O)—O—C(=O)— in a ring), including but not limited to maleic anhydride ($C_5$), succinic anhydride ($C_5$), and glutaric anhydride ($C_6$);

cyclic carbonates (—O—C(=O)—O— in a ring), such as ethylene carbonate ($C_5$) and 1,2-propylene carbonate ($C_5$);

imides (—C(=O)—NR—C(=O)— in a ring), including but not limited to, succinimide ($C_5$), maleimide ($C_5$), phthalimide, and glutarimide ($C_6$);

lactones (cyclic esters, —O—C(=O)— in a ring), including, but not limited to, β-propiolactone, γ-butyrolactone, δ-valerolactone (2-piperidone), and ε-caprolactone;

lactams (cyclic amides, —NR—C(=O)— in a ring), including, but not limited to, β-propiolactam ($C_4$), γ-butyrolactam (2-pyrrolidone) ($C_5$), δ-valerolactam ($C_6$), and ε-caprolactam ($C_7$);

cyclic carbamates (—O—C(=O)—NR— in a ring), such as 2-oxazolidone ($C_5$);

cyclic ureas (—NR—C(=O)—NR— in a ring), such as 2-imidazolidone ($C_5$) and pyrimidine-2,4-dione (e.g., thymine, uracil) ($C_6$).

The above groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound or group as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{5-20}$aryl group (also referred to as a $C_{5-20}$aryloxy group), preferably a $C_{1-7}$alkyl group.

Alkoxy: —OR, wherein R is an alkyl group, for example, a $C_{1-7}$alkyl group. Examples of $C_{1-7}$alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$alkyl group, a $C_{3-20}$heterocyclyl group, or a $C_{5-20}$aryl group, preferably a $C_{1-7}$alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$alkyl group, a $C_{3-20}$heterocyclyl group, or a $C_{5-20}$aryl group, preferably a $C_{1-7}$alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$alkyl group, a $C_{3-20}$heterocyclyl group, or a $C_{5-20}$aryl group, preferably hydrogen or a $C_{1-7}$alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$alkyl group, a $C_{3-20}$heterocyclyl group, or a $CO_{5-20}$aryl group, preferably a $C_{1-7}$alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a $C_{1-7}$alkyl group (also referred to as $C_{1-7}$alkylamino or di-$C_{1-7}$alkylamino), a $C_{3-20}$heterocyclyl group, or a $C_{5-20}$aryl group, preferably H or a $C_{1-7}$alkyl group, or, in the case of a "cyclic" amino group, H and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a $C_{1-7}$alkyl group, a $C_{3-20}$heterocyclyl group, or a $C_{5-20}$aryl group, preferably hydrogen or a $C_{1-7}$alkyl group, and R$^2$ is an acyl substituent, for example, a $C_{1-7}$alkyl group, a $C_{3-20}$heterocyclyl group, or a $C_{5-20}$aryl group, preferably hydrogen or a a $C_{1-7}$alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

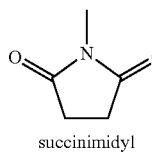 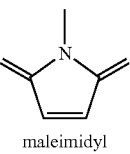 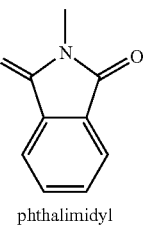
succinimidyl    maleimidyl    phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a $C_{1-7}$alkyl group, a $C_{3-20}$heterocyclyl group, or a $C_{5-20}$aryl group, preferably hydrogen or a $C_{1-7}$alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$ Guanidino: —NH—C(=NH)NH$_2$.

Tetrazolyl: a five membered aromatic ring having four nitrogen atoms and one carbon atom,

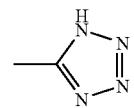

Imino: =NR, wherein R is an imino substituent, for example, for example, hydrogen, a $C_{1-7}$alkyl group, a $C_{3-20}$heterocyclyl group, or a $C_{5-20}$aryl group, preferably H or a $C_{1-7}$alkyl group. Examples of imino groups include, but are not limited to, =NH, =NMe, and =NEt.

Amidine (amidino): —C(=NR)NR$_2$, wherein each R is an amidine substituent, for example, hydrogen, a $C_{1-7}$alkyl group, a $C_{3-20}$heterocyclyl group, or a $C_{5-20}$aryl group, preferably H or a $C_{1-7}$alkyl group. Examples of amidine groups include, but are not limited to, —C(=NH)NH$_2$, —C(=NH)NMe$_2$, and —C(=NMe)NMe$_2$.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$alkyl group (also referred to as a $C_{1-7}$alkylthio group), a $C_{3-20}$heterocyclyl group, or a $C_{5-20}$aryl group, preferably a $C_{1-7}$alkyl group. Examples of $C_{1-7}$alkylthio groups include, but are not limited to, —SCH$_3$ and —SCH$_2$CH$_3$.

Disulfide: —SS—R, wherein R is a disulfide substituent, for example, a $C_{1-7}$alkyl group, a $C_{3-20}$heterocyclyl group, or a $C_{5-20}$aryl group, preferably a $C_{1-7}$alkyl group (also referred to herein as $C_{1-7}$alkyl disulfide). Examples of $C_{1-7}$alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a $C_{1-7}$alkyl group, a $C_{3-20}$heterocyclyl group, or a $C_{5-20}$aryl group, preferably a $C_{1-7}$alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_{1-7}$alkyl group, a $C_{3-20}$heterocyclyl group, or a $C_{5-20}$aryl group, preferably a $C_{1-7}$alkyl group, including, for example, a fluorinated or perfluorinated $C_{1-7}$alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S (=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a $C_{1-7}$alkyl group, a $C_{3-20}$heterocyclyl group, or a $C_{5-20}$aryl group, preferably a $C_{1-7}$alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a $C_{1-7}$alkyl group, a $C_{3-20}$heterocyclyl group, or a $C_{5-20}$aryl group, preferably a $C_{1-7}$alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a $C_{1-7}$alkyl group, a $C_{3-20}$heterocyclyl group, or a $C_{5-20}$aryl group, preferably a $C_{1-7}$alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a $C_{1-7}$alkyl group, a $C_{3-20}$heterocyclyl group, or a $C_{5-20}$aryl group, preferably a $C_{1-7}$alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$alkyl group, a $C_{3-20}$heterocyclyl group, or a $C_{5-20}$aryl group, preferably a $C_{1-7}$alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^8$R$^9$, wherein R$^8$ and R$^9$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^8$R$^9$, wherein R$^8$ and R$^9$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^8$S(=O)$_2$OH, wherein R$^8$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^8$S(=O)$_2$R, wherein R$^8$ is an amino substituent, as defined for amino groups, and R is a sulfonamino substituent, for example, a $C_{1-7}$alkyl group, a $C_{3-20}$heterocyclyl group, or a $C_{5-20}$aryl group, preferably a $C_{1-7}$alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^8$S(=O)R, wherein R$^8$ is an amino substituent, as defined for amino groups, and R is a sulfinamino substituent, for example, a $C_{1-7}$alkyl group, a $C_{3-20}$heterocyclyl group, or a $C_{5-20}$aryl group, preferably a $C_{1-7}$alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$alkyl group, a $C_{3-20}$heterocyclyl group, or a $C_{5-20}$aryl group, preferably a $C_{1-7}$alkyl group or a $C_{5-20}$aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^8$)—NR$^9{}_2$, where R$^8$ and R$^9$ are phosphoramidite substituents, for example, —H, a (optionally substituted) $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^8$)—NR$^9{}_2$, where R$^8$ and R$^9$ are phosphoramidate substituents, for example, —H, a (optionally substituted) $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Silyl: —SiR$_3$, where R is a silyl substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of silyl groups include, but are not limited to, —SiH$_3$, —SiH$_2$(CH$_3$), —SiH(CH$_3$)$_2$, —Si(CH$_3$)$_3$, —Si(Et)$_3$, —Si(iPr)$_3$, —Si(tBu)(CH$_3$)$_2$, and —Si(tBu)$_3$.

Oxysilyl: —Si(OR)$_3$, where R is an oxysilyl substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of oxysilyl groups include, but are not limited to, —Si(OH)$_3$, —Si(OMe)$_3$, —Si(OEt)$_3$, and —Si(OtBu)$_3$.

Siloxy (silyl ether): —OSiR$_3$, where SiR$_3$ is a silyl group, as discussed above.

Oxysiloxy: —OSi(OR)$_3$, wherein OSi(OR)$_3$ is an oxysilyl group, as discussed above.

In many cases, substituents are themselves substituted. For example, a $C_{1-7}$alkyl group may be substituted with, for example:

hydroxy (also referred to as a hydroxy-$C_{1-7}$alkyl group);
halo (also referred to as a halo-$C_{1-7}$alkyl group);
amino (also referred to as a amino-$C_{1-7}$alkyl group);
carboxy (also referred to as a carboxy-$C_{1-7}$alkyl group);
$C_{1-7}$alkoxy (also referred to as a $C_{1-7}$alkoxy-$C_{1-7}$alkyl group);
$C_{5-20}$aryl (also referred to as a $C_{5-20}$aryl-$C_{1-7}$alkyl group)

Similarly, a $C_{5-20}$aryl group may be substituted with, for example:

hydroxy (also referred to as a hydroxy-$C_{5-20}$aryl group);
halo (also referred to as a halo-$C_{5-20}$aryl group);
amino (also referred to as an amino-$C_{5-20}$aryl group, e.g., as in aniline);
carboxy (also referred to as an carboxy-$C_{5-20}$aryl group, e.g., as in benzoic acid);
$C_{1-7}$alkyl (also referred to as a $C_{1-7}$alkyl-$C_{5-20}$aryl group, e.g., as in toluene);
$C_{1-7}$alkoxy (also referred to as a $C_{1-7}$alkoxy-$C_{5-20}$aryl group, e.g., as in anisole);
$C_{5-20}$aryl (also referred to as a $C_{5-20}$aryl-$C_{5-20}$aryl, e.g., as in biphenyl).

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Isomers

Certain compounds may exist in one or more particular geometric, optical, enantiomeric, diasteriomeric, epimeric, atropic, stereoisomeric, tautomeric, conformational, or anomeric forms.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine and amide/imino alcohol.

Salts

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also include salt forms thereof.

Solvates

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

Unless otherwise specified, a reference to a particular compound also include solvate forms thereof.

Various preferred aspects and embodiments of the present invention employ one or more indole compounds selected from the group consisting of isoquinoline, 3-β-indoleacrylic acid, quinoline, indoline and tryptamine.

Compounds that assist the bacterial stress response, such as indole acetic acid (IAA), may be excluded (Bianco et al., 2006), also pyrrole.

A 0.5 M stock solution of indole may conveniently be prepared in ethanol (0.585 g in 10 ml absolute ethanol, although other stock concentrations and other solvents are possible). A volume of the indole stock solution appropriate to achieve the desired final concentration may be added directly to treat cells, for example in a batch culture of cells grown in either shake-flask or a fermenter. For cells grown in fed-batch fermenter culture an appropriate volume of indole stock solution may be introduced via the feed.

In shake-flask culture we have shown that an appropriate final concentration of indole to induce quiescence of E. coli cells is 2 mM. If too little indole is added the cells do not enter quiescence, and if too much is added growth may cease immediately (FIGS. 2a, 2b, 4a) with undesirable consequences for the protein synthetic capacity of the culture (FIG. 4b). It is possible that the concentration of indole required to induce quiescent cells with optimum protein synthetic capacity may vary with the species of bacterium and the growth conditions (growth medium composition, temperature etc). The appropriate concentration may be established by testing the effect of a range of indole concentrations and observing their effect on cell growth and the production of an appropriate test protein.

The cell may be transformed with a heterologous gene of interest for expression. "Transformation" refers to any means of introduction of nucleic acid into a cell. A heterologous gene for expression in the cell may be cloned into an expression vector or it may be introduced directly, as discussed further below.

The heterologous (or "exogenous" or "foreign") gene of interest may be inducible or constitutively expressed. The heterologous gene product may be one which has a toxic effect on the cell, particularly one which adversely affects viability or cell growth and/or division. The heterologous gene may be a non-E. coli gene, or if a non-E. coli host cell is employed a gene not of that host, and it may be a eukaryotic gene e.g. mammalian.

In broth culture cells can in accordance with the invention be grown up and treated with an indole compound to induce a quiescent state in which expression of genes on the condensed chromosomal DNA is eliminated, or reduced, compared with prior to indole treatment. Expression of plasmid vector borne genes proceeds in these cells.

Expression of a gene product which has an adverse effect on cell growth and/or division, for example one which interferes with replication of the bacterial chromosome, transcription of one or more genes essential to the growth and division of the host cell, or disrupts one or more other vital processes, is less likely to have an adverse effect on quiescent (non-growing) cells than growing cells.

According to another aspect, the present invention provides a method of expressing a gene heterologous to a cell, comprising:
(a) growing cells, e.g. hns⁻ cells, in broth culture, the cells containing an extra-chromosomal heterologous gene;
(b) treating the cells with an indole compound and causing or allowing expression of the heterologous gene.

The method may comprise a step of introducing a vector comprising nucleic acid encoding the gene of interest with suitable control elements for transcription and translation.

In various embodiments, the invention provides methods as set out in the claims.

Following production of the heterologous gene product, the method may include any number of conventional purification steps (Harris & Angal, 1989).

The expression product may be isolated and/or purified from cells from the culture or from the broth culture medium. It is conventional in the art to provide recombinant gene products as a fusion with a "signal sequence" which causes secretion of the product into the growth medium, to facilitate purification. This is one possibility amongst the many known to those skilled in the art.

An isolated and/or purified expression product may be modified and the expression product or a modified form thereof may be formulated into a composition which includes at least one additional component, such as a pharmaceutically acceptable excipient, carrier, buffer, stabiliser or other materials well known to those skilled in the art. Such materials should, for a pharmaceutical composition, be non-toxic and should not interfere with the efficacy of the active ingredient. The precise nature of the carrier or other material will depend on the route of administration.

An expression product may be modified for example by chemical derivatisation or cross-linking to one or more other molecules, including peptides, polypeptides, labelling molecules.

A chemical moiety may be introduced at a specific chemically modifiable residue or residues. For instance, a cysteine residue may be available for chemical modification via its thiol group. Other chemically modifiable amino acids include lysine, glutamate, histidine and tyrosine. Covalent modification allows a wide variety of moieties to be incorporated, particularly reporter groups or cofactors for catalysis. This allows the interaction of large organic groups such as the fluorescent reporter group, 7-nitrobenz-2-oxa-1,3-diazole (NBD). Other large groups such as the flavin cofactors for catalysis, FMN and FAD may be incorporated.

There are other possible ways of modifying a polypeptide. There are a number of amino acid residues which may be specifically derivatized using molecules containing specific functional groups. For instance, amino groups may be modified with N-hydroxysuccinimide esters, carboxyl groups with carbodiimides, histidines and cysteines with halomethyl ketones, arginine with glyoxals (see e.g. A. R. Fersht, Enzyme Structure and Mechanism 2nd edn, 1985 pp 248-251, W.H. Freeman, New York).

Some reagents which may be used to modify specific amino-acid residues are given by T. Imoto and H. Yamada in "Protein Function: a Practical Approach", pp 247-277, 1989. To introduce specific functional groups into polypeptides the reactive group of these reagents may be combined with the functional group in a modifying reagent. For instance, if it is desired to modify a protein with the fluorophore 7-amino-4-methylcoumarin-3-acetic acid, the N-hydroxysuccinimidyl ester of the molecule may be used to modify amino groups, whereas N-[6-(-amino-4-methylcoumarin-3-acetamido) hexyl]-3'-(2'-pyridyldithio)propionamide may be used to modify cysteine groups.

Another possible methodology is to use transglutaminase which catalyzes an acyl-transfer reaction between the gamma-carboxyamide group of glutamine residues and primary amines (E. Bendixen et al, J. Biol. Chem. 26821962-21967, 1993; K. N. Lee et al *Biochim. Biophys. Acta* 1202 1-6 1993; T. Kanaji et al *J. Biol. Chem.* 268 11565-11572 1993). This enzyme could therefore introduce amino acid residues from a peptide into a glutamine residue through a peptide lysine epsilon amino group or into a lysine group via a peptide glutamine group. The enzyme could also catalyse derivatization of glutamine residues with a primary amine.

A further approach is to introduce chemical moieties to either the N or C terminus of a polypeptide using reverse proteolysis or chemical conjugation or a combination of the two (I. Fisch et al, *Bioconj. Chem.* 3, 147-153, 1992; H. F. Gaertner et al, *Bioconjug. Chem.* 3, 262-268, 1992; H. F. Gaertner et al, *J. Biol. Chem.* 269, 7224-7230, 1994; J. Bongers et al, *Biochim. Biophys. Acta,* 50, S57-162, 1991; R. Offord, *Protein Engineering,* 4, 709-710, 1991). These methods have been used to introduce non-encoded elements to protein and peptide molecules.

Examples of fluorophores which may be introduced are fluorescein, phycoerythrin, coumarin, NBD, Texas Red™ and chelated lanthanide ions. Examples of catalytic groups which may be introduced are flavin adenine dinucleotide (FAD), flavin mononucleotide (FMN), cytochromes and chelated metal ions such as zinc and copper.

Systems for cloning and expression of a polypeptide in a variety of different host cells are well known.

Suitable vectors can be chosen or constructed, containing appropriate regulatory sequences, including promoter sequences, terminators, polyadenylation sequences, enhancer sequences, marker genes and other sequences as appropriate. Vectors may be plasmids, viral e.g. 'phage, or phagemid, as appropriate. For further details see, for example *Molecular Cloning: a Laboratory Manual:* 3rd edition, Sambrook and Russell, 2001, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Protocols in Molecular Biology,* Second Edition, Ausubel et al. eds., John Wiley & Sons, 1992.

For bacterial cells, suitable techniques for introducing nucleic acid ("transformation") may include calcium chloride transformation, electroporation and transfection using bacteriophage.

The introduction may be followed by causing or allowing expression from the nucleic acid, e.g. by culturing host cells under conditions for expression of the gene.

The term "inducible" as applied to a gene or more particularly a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The desirable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level which brings about the desired phenotype.

For use in bacterial systems, many inducible promoters are known (Old and Primrose, 1994). Common examples include $P_{lac}$ (IPTG), $P_{tac}$ (IPTG), lambda$P_R$ (loss of CI repressor), lambda$P_L$ (loss of CI repressor), $P_{trc}$ (IPTG), $P_{trp}$ (IAA). The inducing agent is shown in brackets after each promoter.

The use of a quiescent cell system in large scale fermenters may have one or more advantages, such as a higher yield of product, a greater purity of product due to lower levels of contamination by host gene products, fewer problems of structural and segregational instability because of the reduced stress on the host cells.

Generally in the art, problems arise when attempting to monitor the products of vector-borne genes, due to the high background of chromosomal gene products. To circumvent these problems, "minicells" and "maxicells" have been used. Both approaches require the use of host cells carrying specific mutations. Minicells are chromosome-less cells produced as a result of asymmetric deposition of the septum (the "cell divider") during cell division. Minicells have to be separated physically from chromosome-containing cells, typically by sucrose gradient centrifugation; a time consuming and technically-demanding procedure. Maxicells carry chromosomal mutations which make them UV-sensitive and are irradiated to fragment the bacterial chromosome; plasmids survive by virtue of their high numbers and their small size. The majority of protein synthesis is therefore from plasmid genes.

Use of the present invention offers a simple and effective alternative to minicells and maxicells. According to another aspect of the invention there is a method of monitoring the production of protein by expression from an extra-chromosomal vector of interest, comprising introducing the vector into host cells and growing the cells in culture, treating the cells with an indole compound to induce quiescence, causing or allowing expression from the vector of interest and determining the expression from the vector. As discussed at length already above, the cells may be hns⁻ or be otherwise sensitive to establishment of quiescence on treatment with indole in broth culture.

Expression at the polypeptide level may be determined by introducing a suitable label into the cells and determining the incorporation of the label into produced peptides or polypeptides. The method may comprise introducing the label into the culture, causing or allowing expression from the vector of interest, lysing cells from the culture, running the lysate on an SDS-polyacrylamide gel and observing the labelled protein on the gel.

The labelled amino acid may be $^{35}$S-methionine. Observation of radiolabelled proteins may be by autoradiography.

Expression at the mRNA level may be similarly determined by using a suitable label.

The vector of interest may in principle be introduced into the cells before or after treatment with an indole compound. However, it is preferred that the vector be introduced before indole compound treatment.

After quiescence is induced, only extra-chromosomal genes within the cells, such as on vectors such as plasmids, will be expressed, or predominantly only these genes. The condensation of the chromosomal DNA upon indole treatment reduces or eliminates expression of chromosomal genes. The protein which can be observed by means of the label will be that produced after "shut-down" of the chromosomes, i.e. that encoded by nucleic acid retained extra-chromosomally in the cells.

One aspect of the present invention is a method to amplify the copy number of plasmid cloning vectors when cells enter the quiescent state. This reduces the metabolic load imposed on cells during the growth phase and increases the copy number of the vector (and thus of the product gene) during the quiescent state. Many plasmid replication control systems are described by the "+n" model which states that for a plasmid with an average copy number of n in a new-born cell, an average of n replication events will occur per unit time (which is the generation time in a steady state culture), irrespective of actual copy number (Nielsen and Molin, 1984). We have discovered that for cells in the quiescent state, replication of some plasmids continues, despite the cessation of cell growth and division. It is thus possible to employ a low copy number vector which places the minimum stress on its host cells during the growth phase of the culture but which increases in copy number during and after entry into quiescence.

Many scientific investigations, including in vivo studies of DNA replication and cell division, are greatly assisted by synchronising the cells within culture so that all cells undergo division at the same time. Existing procedures are technically-demanding or unreliable, involving the isolation of new-born cells by virtue of their size or using a bacteriostatic agent (e.g. the antibiotic chloramphenicol) to block a key process such as the initiation of chromosomal DNA replication and removing the agent by washing after growth has been halted. The reversibility of the block of cell division in accordance with the present invention provides a simple and effective way to achieve synchronisation of cell division and chromosomal DNA replication.

Rcd blocks growth at a specific stage in the cell cycle [Patient & Summers, 1993]; chromosome partitioning is complete but septation has not occurred. The effect is reversible for cells within the population without serious loss of cell viability, subject to how long the culture has been in quiescence. Reversing of quiescence induced by means of an indole compound in accordance with the present invention may be employed in aspects and embodiments of the present invention.

According to a further aspect of the present invention there is provided a method of synchronising cell cycles of cells in broth culture, comprising inducing quiescence within (e.g.) hns⁻ cells in broth culture by treatment of the cells with an indole compound, incubating the cells for a time to achieve quiescence, which may for example be equivalent to a further cell cycle, one and half cell cycles or two cell cycles at least, and removing the indole compound, thereby allowing the cells to exit quiescence.

The present invention further encompasses use of hns⁻ cells or rnc cells in any of the methods described and vectors specially adapted for use in any of the methods.

The use of indole or other indole compound as disclosed for treating bacterial cells to induce quiescence represents an aspect of the present invention.

As noted, the cells made quiescent in accordance with the various aspects and embodiments of the present invention, "chemical Q cells" (cQC) may be used in a number of ways, not limited to but including the following.

Cultures of strains, e.g. wherein a cellular component which normally antagonises quiescence is disrupted, for example hns205 or rnc14 mutant strains, made quiescent by the addition of indole or other indole compound to the culture medium (cQC) may be used for recombinant protein expression in small-scale shake-flask culture, or in batch or fed-batch fermenter culture. Cells may be grown in any appropriate culture medium.

Recombinant protein may be expressed from any suitable expression vector at any convenient culture temperature. If the recombinant protein gene is expressed from a promoter up-regulated in response to indole, the product may be expressed in cQC without the need for an inducing signal (compare this with the use of the lac operon promoter, $P_{lac}$, which requires the addition of IPTG for induction). One such promoter is that of E. coli gene mdtE, which shows a 22-fold elevation of expression in response to 2 mM indole (Hirakawa et al., 2005).

We have further devised an approach to expression in quiescent cells that we term "c-QED" ("chemical Quiescent Cells, Expression Direct").

This application permits the rapid expression of proteins in bacterial cells without the need for inserting the product gene into an expression vector. It was developed initially for use with the Rcd-induced quiescent cell system but is useful with chemical Quiescent Cells. In this method the product gene, incorporated into a direct expression cassette, is introduced into the chemical Quiescent Cells by, for example, transformation or electroporation leading to immediate expression of the product. The direct expression cassette may be a product gene incorporated into a circular or linear DNA molecule. This DNA molecule may be a plasmid if it is capable of autonomous replication but this is not necessary for the c-QED system. The expression cassette may be generated by PCR, using appropriate primers to amplify the gene of interest. In this case it is necessary that the ends of the PCR product are protected from exonuclease-mediated degradation and that appropriate transcription and translation control signals are adjacent to the gene of interest. These objectives may both be achieved by ligating hairpin-loop DNA molecules onto the ends of the PCR product. The hairpin-loop adjacent to sequences coding for the N-terminus of the recombinant protein should include a promoter and a ribosome binding site (RBS). There is no need for such sequences in the hairpin-loop ligated to the end of the PCR product adjacent to sequences encoding the C-terminus of the recombinant protein but a transcription terminator sequence may be included if required. This approach enables the desired protein to be expressed directly from a PCR product, without the need for insertion into an expression vector. It is suitable for small-scale, high-throughput approaches where small amounts of large numbers of recombinant proteins are required. It may also be used for the synthesis of proteins which are toxic to their bacterial host. Using conventional expression systems the gene encoding the toxic protein must be expressed from a promoter which can be tightly repressed up to the time when protein expression is required. Using c-QED this difficulty is avoided because the gene encoding the toxic protein is only introduced into the quiescent cells when its expression is required. It is thus possible to express a highly toxic gene from an constitutively active promoter.

Various further aspects and embodiments will be apparent to those skilled in the art in the light of the present disclosure, including the following experimentation. All documents mentioned anywhere herein are incorporated by reference.

Experimentation

Tryptophanase is Targeted by Rcd

As noted already above, we have shown that a tryptophanase knockout strain of E. coli was insensitive to extremely high levels of Rcd, being resistant to the inhibition of colony formation on solid medium which results from Rcd over-expression. This provided indication that Rcd targets tryptophanase. Subsequently we have demonstrated that an increased level of intracellular indole results when Rcd is expressed in response to multimerization of a cer+ plasmid, or when the Rcd is expressed from an independently-regulated promoter such as $P_{lac}$. Evidence for a direct interaction between Rcd and tryptophanase was provided by our unpublished observations that, (i) in an in vitro assay using purified components, Rcd increases the affinity of tryptophanase for its substrate (tryptophan) approximately four-fold and (ii) using column chromatography, tryptophanase is retained by a column to which Rcd has been linked covalently.

Generation of Quiescent E. coli By Exogenous Indole

Figure 1:
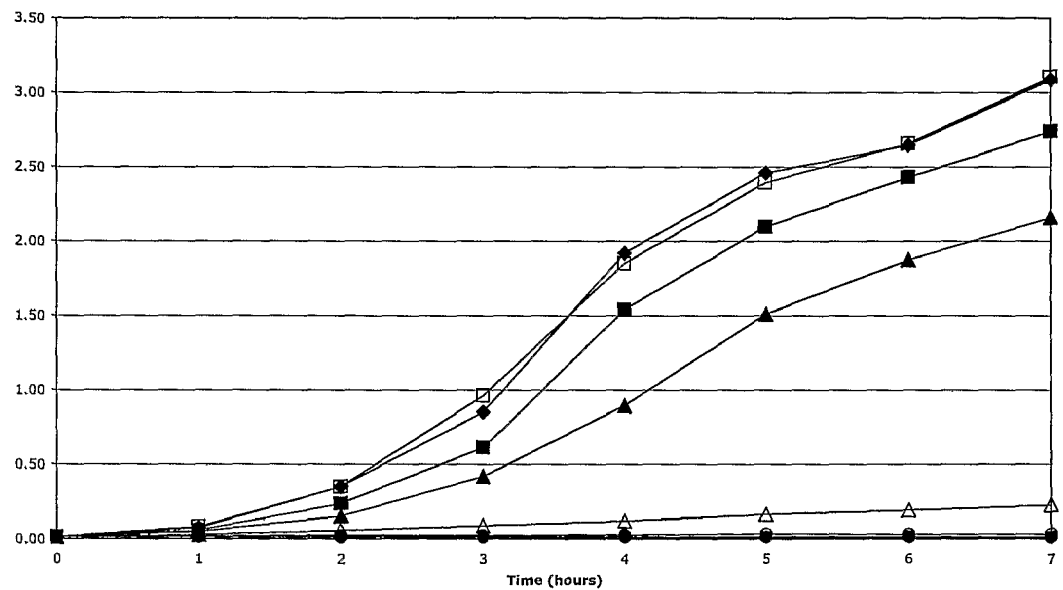
FIG. 1 shows growth inhibition of *E. coli* BW25113 by indole. (open squares, no indole; closed diamonds, 1 mM indole; closed squares, 2 mM indole; closed triangles, 3 mM indole; open triangles, 4 mM indole; open circles, 5 mM indole; closed circles, 6 mM indole)

We have now established that the addition of indole to broth cultures of E. coli inhibits growth (FIG. 1). For E. coli strain BW25113 cultured in L-broth, growth inhibition was not evident at 1 mM indole but partial inhibition was apparent at 2 and 3 mM. Growth inhibition was severe at concentrations of 4 mM or above.

We found that the response of E. coli W3110 cultured in tryptone water broth was qualitatively similar to BW25113 in L-broth (FIG. 2). 2 mM indole caused partial growth inhibition while 4 mM indole inhibited growth severely.

An hns205 mutant of W3110 displayed a different response to indole from its wild-type parent strain (FIG. 2). In tryptone water broth containing 2 mM indole at 37° C., the growth rate of W3110 hns205 declined over approximately 6 hours before entering a non-growing (quiescent) state. We refer to the indole-induced non-growing state of hns205 mutant cells as chemically-induced quiescent cells (cQC).

Entry into the quiescent state is temperature-independent. We were able to induce quiescence by the addition of 2 mM indole at 30° C. and 42° C. (FIG. 3), as well as at 37° C. (FIG. 2). In each case the quiescent state was stable and persisted for at least 24 hours. The phenomenon of "escape" was not witnessed when working with indole-induced quiescent cultures.

To demonstrate the capacity of indole-induced quiescent E. coli for de novo protein expression, we have examined the expression of a cytokine (hGM-CSF; FIG. 4) and beta-galactosidase (LacZ; FIG. 5) in small-scale batch culture of W3110 hns205. Expression of both proteins was observed in indole-treated cultures.

Figure 6:
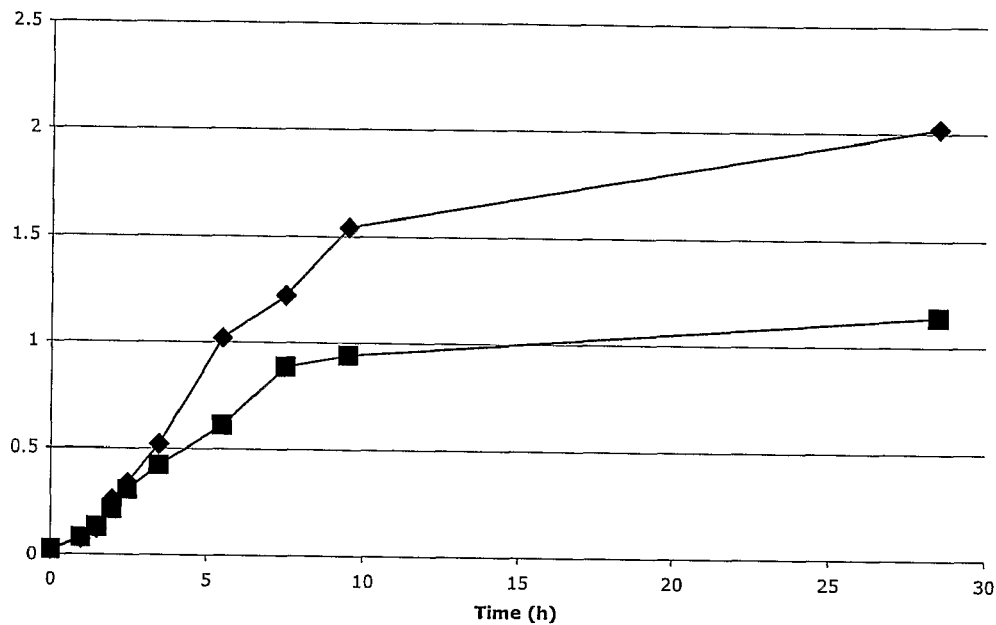
FIG. 6 shows that indole induces quiescence in an rnc mutant of *E. coli* W3110. (diamonds, 0 mM indole; squares, 2 mM indole).

It is known that Rcd-induced quiescence can be achieved in an rnc14 mutant host as well as in an hns205 mutant (Summers & Rowe, 1997). We have shown that 2 mM indole will induce quiescence in an rnc14 mutant of W3110 (FIG. 6).

Figure 7:
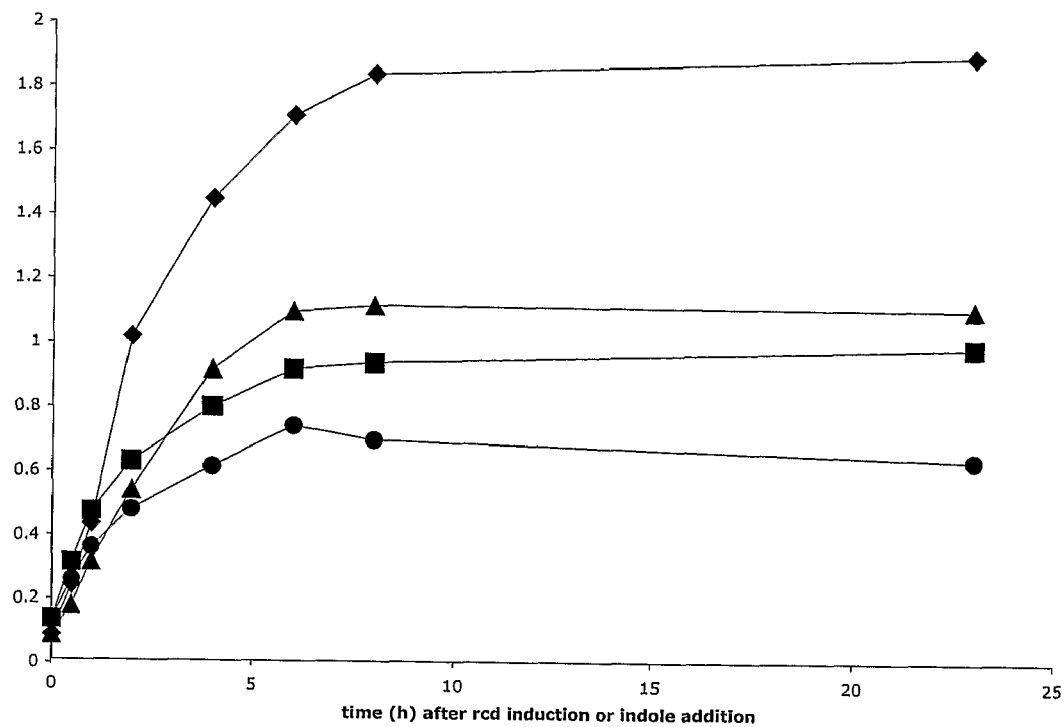
FIG. 7 shows a comparison of indole- and Rcd-induced quiescence of W3110 hns205. (diamonds, W3110 hns205 pcI857ts pUCdelta lacZ+IPTG; triangles, W3110 hns205 pcI857ts pUCdelta lacZ+IPTG+2 mM indole; squares, W3110 hns205 pcI857ts pRcd1+IPTG; circles, W3110 hns205 pcI857ts pRcd1+IPTG+indole)

We compared the response of cultures W3110 hns205 to Rcd over-expression or to the addition of indole (2 mM) to the growth medium (both at 42° C.). The two treatments caused the cultures to enter a quiescent state with similar growth kinetics (FIG. 7).

Materials and Methods, and Further Discussion of Results

For the experimentation for which results are shown in FIG. 1, E. coli BW25113 (Datsenko & Wanner, 2000)was grown overnight at 37° C. in L-broth (Kennedy, 1971). The stationary phase culture was used to inoculate a series of L-broth cultures supplemented with indole (0-6 mM) and their growth was monitored over the next 7 hours.

The addition of 1 mM indole to the culture medium had no effect upon growth. Concentrations of 2 or 3 mM caused a slowing of the growth rate while 4, 5 or 6 mM resulted in almost complete inhibition of growth.

Figure 2A:
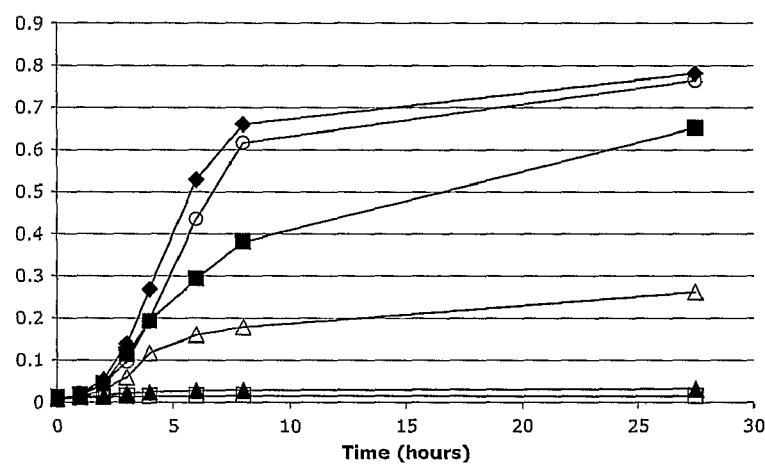
FIG. 2a shows that indole causes tryptone-water broth cultures of W3110 hns205 to enter a quiescent state. (closed diamonds, W3110 0 mM indole; closed squares, W3110 2 mM indole; closed triangles, W3110 4 mM indole; open circles, W3110 hns205 0 mM indole; open triangles, W3110 hns205 2 mM indole; open squares, W3110 hns205 4 mM indole)
Figure 2B:
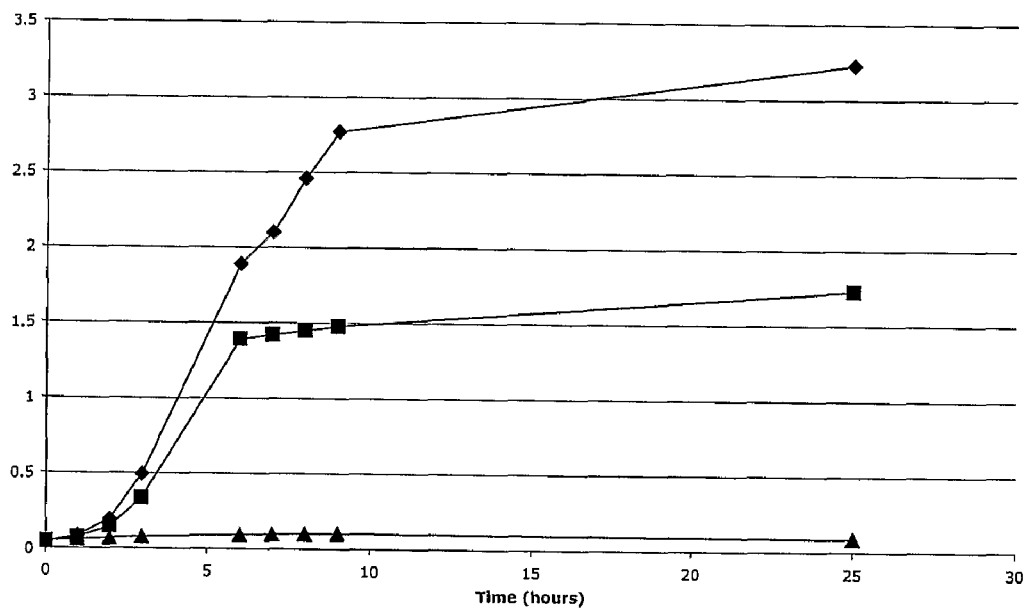
FIG. 2b shows that indole causes L-broth cultures of W3110 hns205 to enter a quiescent state. (diamonds, W3110 hns205 0 mM indole; squares, W3110 hns205 2 mM indole; triangles, W3110 hns205 4 mM indole)

For the experimentation for which results are shown in FIG. 2a and FIG. 2b, W3110 and W3110hns-205 (Mukherjee et al., 2004) were cultured at 37° C. in tryptone water broth (Oxoid) supplemented with 0, 2 or 4 mM indole. W3110 showed a reduced growth rate in response to 2 mM indole although the culture eventually reached a density similar to that of the indole-free control. An indole concentration of 4 mM completely inhibited growth of W3110 (FIG. 2a).

The response of W3110hns-205 to 2 mM indole was distinct from that of its wild-type parent. The culture showed a reduction in growth rate over approx. 6 hours, after which there was very little increase in density. The response of the hns205 mutant to 4 mM indole was similar to that of the parent strain and almost complete inhibition of growth was observed (FIG. 2a). Supplementing the growth medium with 0.5 mM tryptophan made no difference to the response of the cultures to indole.

The response of W3110 hns205 to indole in L-broth was similar to that observed in tryptone water. 2 mM indole caused the culture to enter a quiescent state while 4 mM caused complete growth inhibition (FIG. 2b).

Figure 3A:
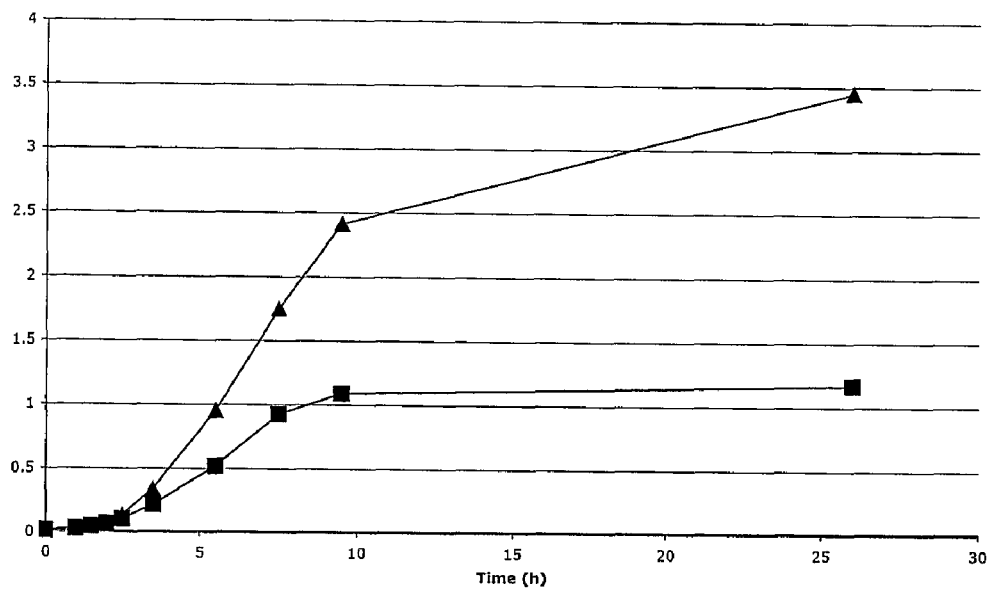
(FIG. 3a (30° C.): triangles, W3110 hns205 0 mM indole; squares, W3110 hns205 2 mM indole.
Figure 3B:
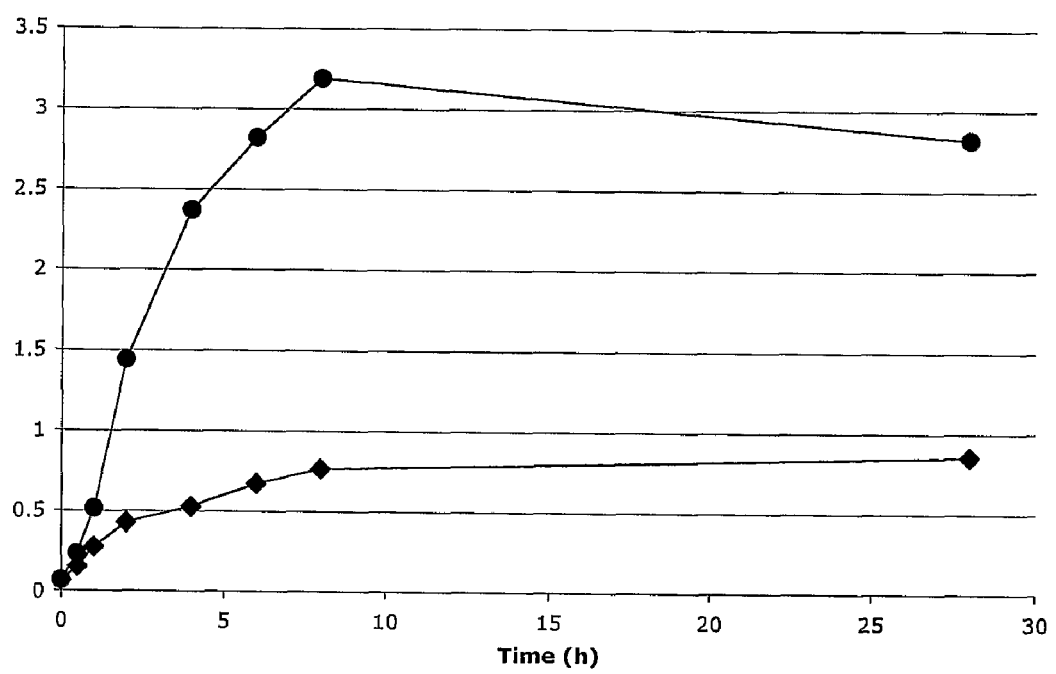
FIG. 3b (42° C.): circles, W3110 hns205 0 mM indole; diamonds, W3110 hns205 2 mM indole.

For the experimentation for which results are shown in FIG. 3a and FIG. 3b, W3110hns205 was cultured in L-broth at 30° C. (FIG. 3a) or 42° C. (FIG. 3b). At t=0 each culture was split into two and indole (final concentration 2 mM) was added to one part. Indole-treated cultures entered the quiescent state with similar kinetics at both temperatures. The control cultures (no indole) continued to grow until they reached stationary phase.

Figure 4A:
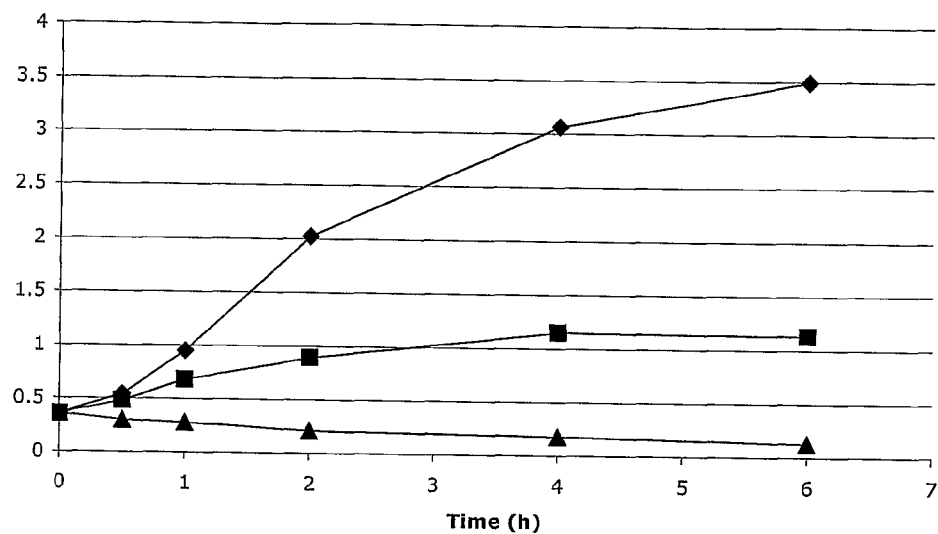
FIG. 4a: Growth ($OD_{600}$) of cytokine-producing cultures (closed diamonds, 0 mM indole; closed squares, 2 mM indole; closed triangles, 4 mM indole).
Figure 4B:
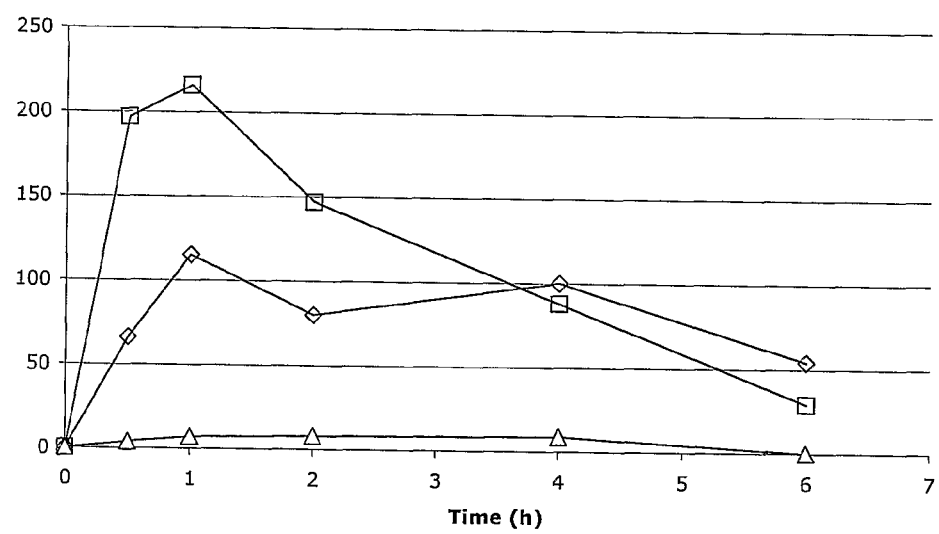
FIG. 4b: cytokine expression (ng ml$^{-1}$ OD$^{-1}$) in indole-treated cultures (open diamonds, 0 mM indole; open squares, 2 mM indole; open triangles, 4 mM indole).

For the experimentation for which results are shown in FIG. 4, W3110hns205 containing plasmid pCMT2bompAhGM-CSF[see below] (which contains the coding sequence for the cytokine hGM-CSF fused to an ompA leader sequence, transcribed from promoter lambda $P_L$ under the control of the temperature sensitive repressor cI857) was grown in L-broth at 30° C. to an $OD_{600}$ of 0.36, at which point the culture was transferred to 42° C. to induce cytokine expression. Simultaneously indole was added to the growth medium at final concentrations of 0, 2 or 4 mM (FIG. 4a).

Cytokine production was quantified by ELISA of total cell lysates and assay data were normalised for culture density (FIG. 4b). Cultures treated with 4 mM indole (which had stopped growing immediately upon indole addition) produced no hGM-CSF. The addition of 2 mM indole established a quiescent state and in these cultures hGM-CSF increased rapidly for the first hour although the protein concentration declined thereafter. In the control culture (no indole), hGM-CSF increased in the first hour before declining. The peak concentration was less than half that seen in the quiescent culture.

Plasmid pCMT2bompAhGM-CSF was generated as follows: The hGM-CSF gene, with an ompA leader sequence, expressed from the lambda$P_L$ promoter, was excised from plasmid A235 (supplied by Amy Isaacson, R&D Systems) by a SalI and BamHI double digest. The approx. 800 bp product was inserted into pCMT2b (Mukherjee et al., 2004) also cut with SalI and BamHI.

Figure 5A:
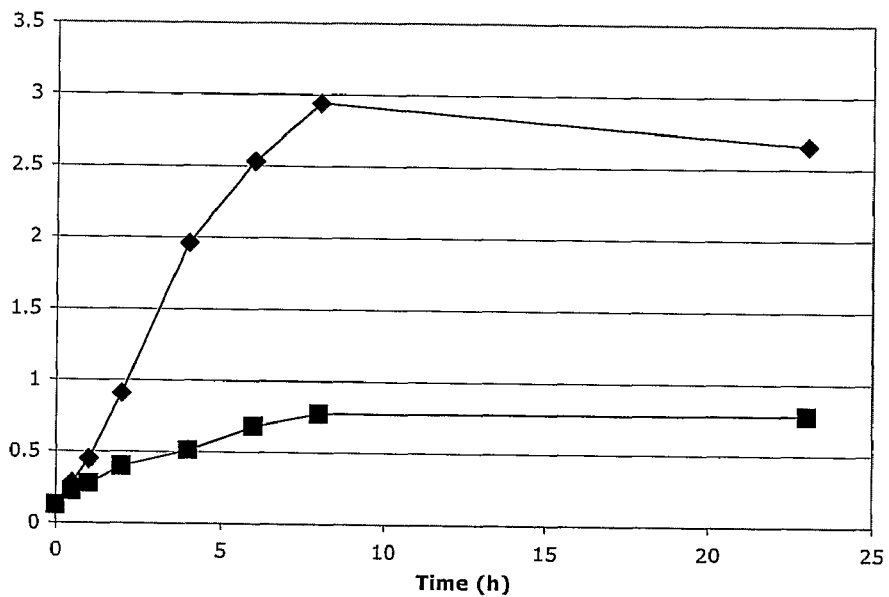
FIG. 5a: Growth ($OD_{600}$) of LacZ-producing cultures (closed diamonds, 0 mM indole; closed squares, 2 mM indole).
Figure 5B:
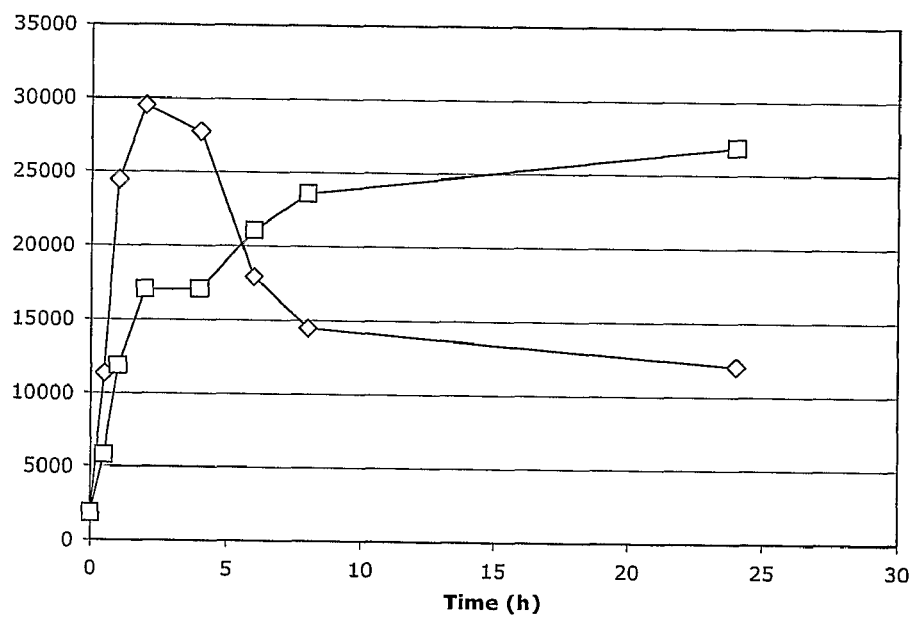
FIG. 5b: LacZ expression in indole-treated cells (open diamonds, 0 mM indole; open squares, 2 mM indole).

For the experimentation for which results are shown in FIGS. 5a and 5b, W3110hns-205 containing pCMT2blacZ (a plasmid which contains the coding sequence for beta-galactosidase, transcribed from promoter lambda $P_L$ under the control of the temperature sensitive repressor cI857) was grown in L-broth at 30° C. to $OD_{600}$=0.15. The culture was then divided into two and the temperature was increased to 42° C. to induce lacZ expression. Indole (2 mM) was added immediately to one subculture to induce a quiescent state, while the other was an indole-free control. Beta-galactosidase activities were measured for 24 hours after the temperature shift.

The growth of the two cultures at 42° C. is shown in FIG. 5a. The indole-treated culture of W3110hns-205 pCMT2blacZ entered a quiescent state, reaching a final $OD_{600}$ of 0.78, while the control culture continued to grow and reached a final $OD_{600}$ of 2.9. For both cultures an induction of beta-galactosidase expression was monitored at 42° C. (FIG. 5b). For the control culture beta-galactosidase activity increased rapidly for two hours after transfer to 42° C., reaching just under 30,000 MU before decreasing to a level of 12,000 MU after 24 h. In the quiescent culture beta-galactosidase showed a more gradual and sustained increase, reaching 27,000 MU after 24 h.

For the experimentation for which results are shown in FIG. 6, a culture of W3110 rnc-14 was grown in L-broth at 37° C. to a density of $OD_{600}$=0.15. The culture was divided into two (t=0) and indole (2 mM) was added to one of the sub-cultures. Growth of the cultures was measured over the following 27 hours. While the control culture eventually reached stationary phase at $OD_{600}$=2, the indole-treated culture entered a non-growing state after approximately 7 hours and remained at a density of $OD_{600}$=1 (approx.). Thus an rnc-14 mutant strain enters quiescence in response to indole with kinetics similar to an hns205 mutant.

The experiment for which results are shown in FIG. 7 compared the growth kinetics of Rcd-induced and indole-induced quiescent cultures. Cultures of W3110hns-205 pcIts[857] (Remaut et al., 1983) transformed with either pRcd1 (Rcd expression plasmid; Mukherjee et al., 2004)) or pUCdeltalacZ (control plasmid; no Rcd) were grown in L-broth at 30° C. for 90 minutes, then 2×5 ml aliquots of each culture were transferred to 50 ml conical flasks, pre-warmed to 42° C. (t=0). The temperature shift induces Rcd expression in cultures containing plasmid pRcd1 but not in cultures containing pUCdeltalacZ. For each pair of cultures, indole (final concentration 2 mM) was added to one of them. IPTG was added to all cultures so that the induction of chromosomal LacZ could be monitored. Culture density was monitored over the following 24 h.

W3110hns-205 pcIts[857] pUCdeltalacZ (no indole, no Rcd) grew normally to stationary phase. W3110hns205 pcIts[857] pRcd1 and W3110hns-205 pcIts[857] plus indole (2 mM) both entered a quiescent state, showing similar kinetics and final cell densities. W3110hns205 pcIts[857] pRcd1 plus indole (2 mM) also entered a quiescent state but more rapidly and reached a lower final density.

pUCdeltalacZ is pUC18 (Yanisch-Perron et al., 1985) with the lacZ fragment and MCS (between co-ordinates 306 and 628) removed by PvuII digestion followed by self-ligation.

The Effect of Indole Compounds on the Induction of Quiescence IN E. Coli W3110HNS-205::TN10

As described above, the addition of indole to the culture medium of E. coli W3110hns-205::Tn10 induces quiescence. We examined the effect of eight indole compounds on growth of E. coli in broth culture and found that isoquinoline and 3-β-indoleacrylic acid had very similar effects to indole.

Quinoline, indoline and tryptamine caused some inhibition of growth but their effect was less severe than indole. Pyrrole and indole acetic acid were not observed to have a significant effect on growth.

Materials and Methods

A single E. coli colony (W3110 hns-205::Tn10) was picked from an L-agar plate containing tetracycline (10 μg ml$^{-1}$) and inoculated into 10 ml L-broth. This was grown overnight in a shaking incubator at 37° C. 200 μl of overnight culture was inoculated into 20 ml L-broth in a 50 ml conical flask, and grown at 37° C. in a shaking water bath to an optical density at 600 nm ($OD_{600}$) of between 0.2 and 0.3. Two ml of this culture was inoculated into 18 ml pre-warmed L-broth containing tetracycline (10 μg ml$^{-1}$) to which had been added an appropriate volume of indole, isoquinoline, indoline, tryptamine, quinoline, or pyrrole stock solution (0.5 M in ethanol), IAA stock solution (0.5 M in water), 3-β-indoleacrylic acid stock solution (0.125 M in ethanol) or 1-acetylindoline stock solution (0.25 M in ethanol) to give a final concentration of 3 mM. (3 mM indole is the minimum concentration which causes immediate growth inhibition of E. coli in L-broth containing tetracycline.) Appropriate control experiments were performed to ensure that the ethanol introduced as the solvent for indole and related compounds (final conc. either 0.6 or 2.4%) was not affecting the growth of the culture.

See Table 1 for compound structures.

Results

Figure 8:
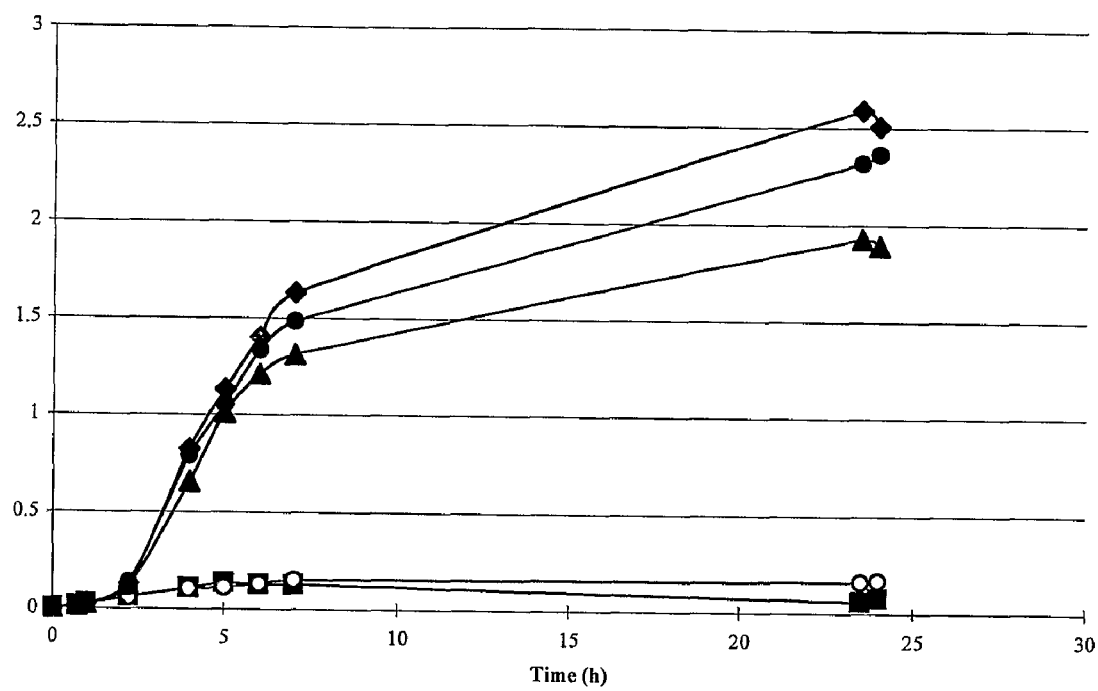
FIG. 8 shows the effect of 3 mM indole, isoquinoline, and indoline on W3110hns-205::Tn10. Growth in L-broth containing tetracycline was monitored by measuring $OD_{600}$ of culture samples. A control (ethanol, 0.6%) was included to ensure that the ethanol used to prepare stock solutions of indole and indole-related compounds was not affecting growth. Data plotted are the mean of two independent assays.

Table 2 summarises the effect of indole and related compounds (each at a final concentration of 3 mM) on the growth of E. coli W3110 hns205 in L-broth containing tetracycline. Detailed growth data are given in FIGS. 8-11. Isoquinoline (FIG. 8) and 3-β-indoleacrylic acid (FIG. 11) had very similar effects to indole. Quinoline (FIG. 10) and 1-acetylindoline (FIG. 11) showed substantial growth inhibition, but less severe than that shown by indole. Indoline (FIG. 8) and tryptamine (FIG. 9) exhibited slight growth inhibition, while pyrrole (FIG. 10) had no observed inhibitory effect at the concentration employed, and IAA (FIG. 9) caused slight stimulation of growth. The latter observation is consistent with reports in the literature that IAA assists the bacterial stress response (Bianco et al., 2006).

CONCLUSION

The results indicate that indole compounds such as isoquinoline, 3-β-indoleacrylic acid, quinoline and 1-acetylindoline show significant inhibitory effects in the growth of E. coli W3110 hns205 and therefore provide alternatives to indole for the establishment of the quiescent state in broth culture. Other alternative compounds may be identified simply by following the testing regime described above.

TABLE 1

Structures of indole-related compounds tested for their effect on the growth of E. coli W3110hns-205::Tn10

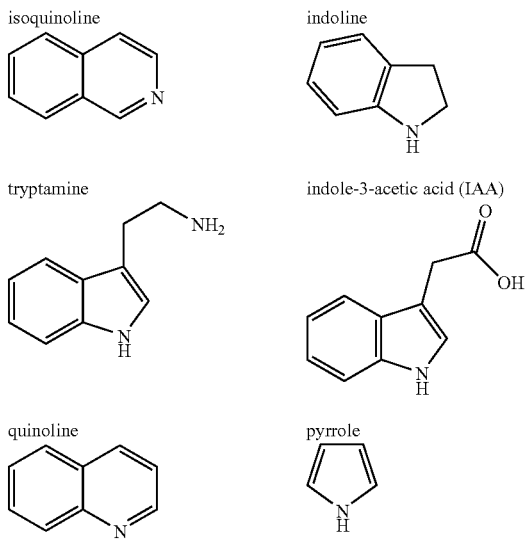

isoquinoline indoline tryptamine indole-3-acetic acid (IAA)

quinoline pyrrole

TABLE 1-continued

Structures of indole-related compounds tested for their effect on the growth of *E. coli* W3110hns-205::Tn10

3-β-indoleacrylic acid      1-acetylindoline

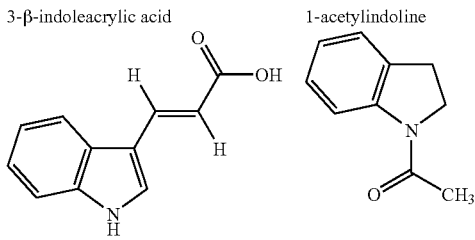

TABLE 2

Summary of the effect of indole and related compounds on W3110hns-205::Tn10.

| Compound | Stock Solution | Growth inhibition[a] |
|---|---|---|
| indole | 0.5 M in ethanol | +++ |
| isoquinoline | 0.5 M in ethanol | +++ |
| indoline | 0.5 M in ethanol | + |
| tryptamine | 0.5 M in ethanol | + |
| IAA | 0.5 M in water | −[b] |
| quinoline | 0.5 M in ethanol | ++ |
| pyrrole | 0.5 M in ethanol | − |
| 3-β-indoleacrylic acid | 0.125 M in ethanol | +++ |
| 1-acetylindoline | 0.25 M in ethanol | ++ |

[a]Semi-quantitative estimate of growth inhibition: +++ indicates that inhibition was equivalent to that seen with indole; − indicates that there was no detectable effect on growth.
[b]The addition of IAA resulted in slight growth stimulation.

REFERENCES

Baneyx (1999) *Current Opinion in Biotechnology* 10, 411-421.
Bianco et al. Arch Microbiol 185, 373-382.
Datsenko & Wanner (2000) *PNAS* 97, 6640-6645.
Flickinger & Rouse (1993) *Biotechnology Progress* 9, 555-572.
Hirakawa et al. (2005) *Molecular Microbiology* 55, 1113-1126.
Kaprelyants et al. (1993) *FEMS Microbiology Reviews* 104, 271-286.
Kennedy (1971) *J Bacteriol* 108, 10-19.
Matin (1992) *J Appl Bacteriol Symp Suppl* 73, 49S-57S.
Mukherjee et al. (2004) *Applied and Environmental Microbiology* 70, 3005-3012.
Patient & Summers (1993) *Mol Microbiol* 8, 1089-1095.
Remaut et al. (1983) *Gene* 22, 103-113.
Rowe & Summers (1999) *Applied and Environmental Microbiology* 65, 2710-2715.
Sharpe et al. (1999) *Microbiology* 145, 2135-2144.
Summers & Rowe (1997 WO97/34996
Tunner et al. (1992) *Biotechnology and Bioengineering* 40, 271-279.
Wang et al. (2001) *J Bacteriol* 183, 4210-4216.
Yanisch-Perron et al. (1985) *Gene* 33, 103-119.

The invention claimed is:

1. A method of producing quiescent cells, the method comprising treating bacterial cells with at least 1 mM indole, wherein the cells are hns− bacterial cells.

2. A method according to claim 1 wherein the cells have a rnc mutation.

3. A method according to claim 1 wherein the cells are *E. coli*.

4. A method according to claim 1 wherein the cells are growing in broth culture prior to treatment with indole.

5. A method according to claim 1 wherein the cells contain an extra-chromosomal heterologous gene prior to treatment with indole, the method comprising causing or allowing expression of the heterologous gene in the quiescent cells.

6. A method according to claim 5 wherein the heterologous gene is under control of an inducible promoter, and expression of the heterologous gene is induced after the cells enter quiescence.

7. A method according to claim 5 wherein the heterologous gene is under control of a promoter that is up-regulated in response to indole.

8. A method according to claim 1 comprising introducing a heterologous gene into the quiescent cells and causing or allowing expression from the heterologous gene in the quiescent cells.

9. A method for producing a gene product from bacterial cells containing an extra-chromosomal heterologous gene encoding the gene product, the method comprising:
   growing in broth culture bacterial cells containing the heterologous gene;
   treating the cells with at least 1 mM indole to induce quiescence in the cell; and
   causing or allowing expression of the heterologous gene in the quiescent cells,
wherein the cells are hns− bacterial cells.

10. A method according to claim 9 comprising, prior to growing the cells in broth culture, a step of introducing the heterologous gene into the bacterial cells.

11. A method for producing a gene product from bacterial cells containing an extra-chromosomal heterologous gene encoding the gene product, the method comprising:
   growing in broth culture bacterial cell;
   treating the cells with at least 1 mM indole to induce quiescence in the cell;
   introducing into the quiescent cells the heterologous gene; and
   causing or allowing expression of the heterologous gene in the quiescent cells,
wherein the cells are hns− bacterial cells.

12. A method according to claim 5 wherein expression from the heterologous gene results in production of a gene product encoded by the heterologous gene, the method further comprising isolating the gene product from the cells, or cell culture.

13. A method according to claim 5 wherein the heterologous gene encodes a gene product that is toxic for the cells, or adversely affects viability, cell growth and/or cell division of the cells.

14. A method according to claim 12 further comprising modifying the gene product and/or formulating the gene product into a composition which includes at least one additional component.

15. A method of monitoring expression from an extrachromosomal gene of interest, the method comprising:
   introducing the gene into bacterial cells;
   growing the cells in broth culture;

treating the cells with at least 1 mM indole to induce quiescence in the cells;
causing or allowing expression from the gene of interest; and
determining expression in the cell,
wherein the introducing of the gene into the cells is before, along with or after the treating with indole to induce quiescence, and wherein the cells are hns⁻ bacterial cells.

16. A method according to claim 15 wherein mRNA production is determined.

17. A method according to claim 15 wherein polypeptide production is determined.

18. A method according to claim 17 wherein polypeptide production is determined by observing polypeptide on an electrophoretic gel.

19. A method for amplifying the copy number of an extra-chromosomal gene of interest in bacterial cells, the method comprising:
introducing the gene into bacterial cells;
growing the cells in broth culture; and
treating the cells with at least 1 mM indole to induce quiescence,
wherein the introducing of the gene into the cells is before, along with or after the treating with indole to induce quiescence, and wherein the cells are hns⁻ bacterial cells.

20. A method according to claim 19 further comprising isolating the extra-chromosomal gene from one or more cells taken from the broth culture.

21. A method of synchronising cell cycles of cells, the method comprising:
treating bacterial cells in broth culture with at least 1 mM indole;
incubating the cells to achieve quiescence; and
removing indole from the culture to allow resumption of growth of the cells,
wherein the cells are hns⁻ bacterial cells.

22. A method according to claim 21 wherein the cells are *E. coli*.

23. A method according to claim 1 wherein the indole is selected from the group consisting of indole, isoquinoline, 3-β-indoleacrylic acid, quinoline, indoline and tryptamine.

24. A method according to claim 9 wherein the indole is selected from the group consisting of indole, isoquinoline, 3-β-indoleacrylic acid, quinoline, indoline and tryptamine.

25. A method according to claim 11 wherein the indole is selected from the group consisting of indole, isoquinoline, 3-β-indoleacrylic acid, quinoline, indoline and tryptamine.

26. A method according to claim 15 wherein the indole is selected from the group consisting of indole, isoquinoline, 3-β-indoleacrylic acid, quinoline, indoline and tryptamine.

27. A method according to claim 19 wherein the indole is selected from the group consisting of indole, isoquinoline, 3-β-indoleacrylic acid, quinoline, indoline and tryptamine.

28. A method according to claim 21 wherein the indole is selected from the group consisting of indole, isoquinoline, 3-β-indoleacrylic acid, quinoline, indoline and tryptamine.

* * * * *